(12) United States Patent
Braun et al.

(10) Patent No.: US 8,648,052 B2
(45) Date of Patent: Feb. 11, 2014

(54) PREVENTION OF CHLAMYDIA INFECTION USING SIRNA

(75) Inventors: Jonathan Braun, Tarzana, CA (US); Lynn K. Gordon, Tarzana, CA (US); Kaori Shimazaki, Los Angeles, CA (US); Madhuri Wadehra-Dhawan, Fontana, CA (US); Kathy A. Kelly, Pacific Palisades, CA (US)

(73) Assignee: The Regents of the University of California, Oakland, CA (US)

(*) Notice: Subject to any disclaimer, the term of this patent is extended or adjusted under 35 U.S.C. 154(b) by 815 days.

(21) Appl. No.: 11/868,788

(22) Filed: Oct. 8, 2007

(65) Prior Publication Data

US 2008/0181889 A1 Jul. 31, 2008

Related U.S. Application Data

(63) Continuation-in-part of application No. PCT/US2006/014238, filed on Apr. 14, 2006.

(60) Provisional application No. 60/671,755, filed on Apr. 15, 2005.

(51) Int. Cl.
*C12N 15/11* (2006.01)
*A61K 39/118* (2006.01)

(52) U.S. Cl.
USPC .................................... 514/44 A; 424/263.1

(58) Field of Classification Search
None
See application file for complete search history.

(56) References Cited

U.S. PATENT DOCUMENTS

| | | | |
|---|---|---|---|
| 5,786,362 | A | 7/1998 | Krongrad |
| 6,506,781 | B1 | 1/2003 | Cobb et al. |
| 6,750,015 | B2 | 6/2004 | Horwitz et al. |
| 6,794,378 | B2 | 9/2004 | Iino et al. |
| 7,229,770 | B1 | 6/2007 | Price et al. |
| 7,288,531 | B2 | 10/2007 | Pal et al. |
| 7,304,042 | B2 | 12/2007 | Pal et al. |
| 7,345,027 | B2 | 3/2008 | Tolentino et al. |
| 7,504,385 | B2 | 3/2009 | Binetti et al. |
| 7,511,025 | B2 | 3/2009 | Wyatt et al. |
| 7,517,865 | B2 | 4/2009 | Meyers |
| 7,521,431 | B2 | 4/2009 | Reich et al. |
| 7,585,848 | B2 | 9/2009 | Masuda et al. |
| 7,592,325 | B2 | 9/2009 | Jimenez et al. |
| 7,629,323 | B2 | 12/2009 | Surmeier et al. |
| 7,638,482 | B2 | 12/2009 | LaVallie et al. |
| 2003/0228305 | A1 | 12/2003 | Frantz et al. |
| 2004/0175385 | A1 | 9/2004 | Marks et al. |
| 2007/0065889 | A1 | 3/2007 | Roberts et al. |

FOREIGN PATENT DOCUMENTS

| | | |
|---|---|---|
| WO | WO 03/057160 A2 | 7/2003 |
| WO | WO 2005/055808 | 6/2005 |
| WO | WO 2006/094014 A2 | 9/2006 |
| WO | WO 2006/094014 A3 | 9/2006 |

OTHER PUBLICATIONS

Chen et al, Pharmacutical Research, 25; pp. 72-86, 2008).*
Schubert et al ; Journal of Molecular Biology vol. 348, Issue 4, May 13, 2005, pp. 883-893.*
Ge et al ; Virus Research vol. 102, Issue 1, Jun. 1, 2004, pp. 37-42.*
Rossi; Gene Therapy (2006) 13, 1493-1494.*
Swanson et al ; Infect .Immunol. Dec. 2007;75(12):5669-77. Epub 2007.*
Devevoye et al ; PLoS Pathog. Mar. 2008; 4(3): e1000022.*
Lane et al ; PLoS Pathog. Mar. 2008;4(3):e1000014.*
Carey , Am J Reprod Immunol. Feb. 28, 2010 Abstract only.*
Amarzguioui, M. et al., "An algorithm for selection of functional siRNA sequences," *Biochemical and Biophysical Research Communications*, (2004) 316:1050-1058.
Anderson, E.M. et al., "Experimental validation of the importance of seed complement frequency to SiRNA specificity," *RNA*, (2008) 14:853-861.
Birmingham, A. et al., "3' UTR seed matches, but not overall identity, are associated with RNAi off-targets," *Nature Methods*, (Mar. 2006) 3(3):199-204.
Cui, W. et al., "OptiRNAi, an RNAi design tool," *Computer Methods and Programs in Biomedicine* (2004) 75:67-73.
Dudek, P., et al., "TROD: T7 RNAi Oligo Designer," *Nucleic Acids Research* (2004) 32:W121-W123.
Elbashir, S.M. et al., "Analysis of gene function in somatic mammalian cells using small interfering RNAs," *Methods* (2002) 26:199-213.
Flynn, M. A. et al., Efficient delivery of small interfering RNA for inhibition of IL-12p40 expression in vivo, *Journal of Inflammation* (2004) 1:4.
Henschel, A. et al., DEQOR: a web-based tool for the design and quality control of siRNAs, *Nucleic Acids Research* (2004) 32:W113-W120.
Hsieh, A. C. et al., "A library of siRNA duplexes targeting the phosphoinositide 3-kinase pathway: determinants of gene silencing for use in cell-based screens," *Nucleic Acids Research* (2004) 32(3):893-901.
Jackson, A. L., et al., "Position-specific chemical modification of siRNAs reduces 'off-target' transcript silencing," *RNA* (2006) 12:1197-1205.
Kim, B. et al., Inhibition of Ocular Angiogenesis by siRNA Targeting Vascular Endothelial Growth Factor Pathway Genes, *American Journal of Pathology* (Dec. 2004) 165(6):2177-2185.
Levenkova, N. et al., "Gene specific siRNA selector," *Bioinformatics* (2004) 20(3): 430-432.

(Continued)

*Primary Examiner* — Padma V Baskar
(74) *Attorney, Agent, or Firm* — Morgan, Lewis & Bockius LLP; Annette S. Parent

(57) ABSTRACT

The present invention provides methods and compositions useful in the treatment or prevention of *Chlamydia* infections. The methods and compositions inhibit the entry of *Chlamydia* into a host cell expressing EMP2 by interfering with the interaction between the *Chlamydia* and EMP2. The compositions include EMP2 nucleic acids and polypeptides as well as anti-EMP2 antibodies.

11 Claims, 11 Drawing Sheets

(56) References Cited

OTHER PUBLICATIONS

Luo, K. Q. et al., "The gene-silencing efficiency of siRNA is strongly dependent on the local structure of mRNA at the targeted region," *Biochemical and Biophysical Research Communications* (2004) 318:303-310.

Ma, Z. et al., Cationic lipids enhance siRNA-mediated interferon response in mice, *Biochemical and Biophysical Research Communications* (2005) 330:755-759.

Milhavet, O. et al., "RNA Interference in Biology and Medicine," *Pharmacol Rev* (2003) 55:629-648.

Morales, S. A. et al., FAK Activation and the Role of Epithelial Membrane Protein 2 (EMP2) in Collagen Gel Contraction, *IOVS*, (Jan. 2009) 50(1):463-469.

Morales, S. A., "Functional Consequences of Interactions between FAK and Epithelial Membrane Protein 2 (EMP2)," *IOVS*, (Oct. 2009) 50(10):4949-4956.

Morrissey, David V. et al., "Activity of Stabilized Short Interfering RNA in a Mouse Model Hepatitis B Virus Replication," *Hepatology* (Jun. 2005) 41(6):1349-1356.

Morrissey, David V. et al., Potent and persistent in vivo anti-HBV activity of chemically modified siRNAs, *Nature Biology* (Aug. 2005) 23(8):1002-1007.

Naito, Y. et al., "siDirect: highly effective, target-specific siRNA design software for mammalian RNA interference," *Nucleic Acids Research* (2004) 32:W124-W129.

Pancoskca, P. et al., "Efficient RNA interference depends on global context of the target sequence: quantitative analysis of silencing efficiency using Eulerian graph representation of siRNA," *Nucleic Acids Research* (2004) 32(4):1469-1479.

Reich, S. J. et al., "Small interfering RNA (siRNA) targeting VEGF effectively inhibits ocular neovascularization in a mouse model," *Molecular Vision* (2003) 9:210-216.

Reynolds, A. et al., "Rational siRNA design for RNA interference," *Nature Biology* (Mar. 2004) 22(3):326-330.

Schiffelers, R. M. et al., "Cancer siRNA therapy by tumor selective delivery with ligand-targeted sterically stabilized nanoparticle," *Nucleic Acids Research* (2004) 32(19):e149.

Shimazaki, K. et al., "Blockade of epithelial membrane protein 2 (EMP2) abrogates infection of *Chlamydia muridarum* murine genital infection model," *FEMS Immunol Med Microbiol* (2008) 1-10.

Shimazaki, K. et al., Epithelial membrane protein 2 modulates infectivity of *Chlamydia muridarum* (MoPn), *Microbes and Infection* (2007) 9:1003-1010.

Soutschek, J. et al., "Therapeutic silencing of an endogenous gene by systemic administration of modified siRNAs," *Nature* (Nov. 2004) 432:173-178.

Takasaki, S. et al., "An Effective Method for Selecting siRNA Target Sequences in Mammalian Cells," *Cell Cycle* (Jun. 2004) 3(6):790-795.

Taxman, D. J. et al., "Criteria for effective design, construction, and gene knockdown by shRNA vectors," *BMC Biotechnology* (2006) 6:7.

Ui-Tei, K. et al., "Guidelines for the selection of highly effective siRNA sequences for mammalian and chick RNA interference," *Nucleic Acids Research* (2004) 32(3):936-948.

Verma, U. N. et al., "Small Interfering RNAs Directed against β-Catenin Inhibit the in Vitro and in Vivo Growth of Colon Cancer Cells," Clinical Cancer Research (Apr. 2003) 9:1291-1300.

Wadehra, M. et al., "The Tetraspan Protein EMP2 Modulates the Surface Expression of Caveolins and Glycosylphosphatidyl Inositol-linked Proteins," *Molecular Biology of the Cell* (May 2004) 15:2073-2083.

Wang, C. et al., "Epithelial membrane protein 2,a 4-transmembrane protein that suppresses B-cell lymphoma tumorigenicity," *Blood* (Jun. 2001) 97(12):3890-3895.

Wang, L., et al., "A Web-based design center for vector-based siRNA and siRNA cassette," *Bioinformatics* (2004) 20(11):1818-1820.

Xia, H. et al., "siRNA-mediated gene silencing in vitro and in vivo," *Nature Biotechnology* (Oct. 2002) 20:1006-1010.

Yano, J. et al., "Antitumor Activity of Small Interfering RNA/Cationic Liposome Complex in Mouse Models of Cancer," *Clinical Cancer Research* (Nov. 2004) 10:7721-7726.

Yuan, B. et al., "siRNA Selection Server: an automated siRNA oligonucleotide prediction server," *Nucleic Acids Research* (2004) 32:W130-W134.

Zhang, Y. et al., "Intravenous RNA Interference Gene Therapy Targeting the Human Epidermal Growth Factor Receptor Prolongs Survival in Intracranial Brain Cancer," *Clinical Cancer Research* (Jun. 2004) 10:3667-3677.

International Search Report mailed on Oct. 13, 2009, for PCT Application No. PCT/US08/79244, 14 pages.

Abrami, L. et al., "Cross-talk between Caveolae and Glycosylphosphatidylinositol-rich Domains", *Journal of Biological Chemistry*, vol. 276, No. 33, pp. 30729-30736 (2001).

Agrawal et al., "Antisense therapeutics: is it as simple as complementary base recognition?" *Molecular Medicine Today*, vol. 6, pp. 72-81 (2000).

Bersinger, N.A., et al., "Production of endometrial placental protein 14 and prolactin by cultured endometrial explants after collagenase and freeze/thaw treatment, and in response to progesterone", *Early Pregnancy: Biology and Medicine*, vol. 1, pp. 134-140 (1995).

Chen, Y. et al., "RNAi for Treating Hepatitis B Viral Infection", *Pharmaceutical Research*, vol. 25, No. 1, pp. 72-86 (2008).

Colman, "Effects of amino acid sequence changes on antibody-antigen interactions" *Research in Immunology*, vol. 145, pp. 33-36 (1994).

Delevoye, C. et al., "SNARE Protein Mimicry by an Intracellular Bacterium", *PLOS Pathogens*, vol. 4, Issue 3, (2008).

Ge, Q. et al., "Use of siRNAs to prevent and treat influenza virus infection", *Virus Research*, vol. 102, pp. 37-42 (2004).

Gura, "Systems for Identifying New Drugs Are Often Faulty" *Science*, vol. 278, pp. 1041-1042 (1997).

Jain, "Barriers to Drug Delivery in Solid Tumors" *Scientific American*, July, pp. 58-65 (1994).

Jen et al., "Suppression of Gene Expression by Targeted Disruption of Messenger RNA: Available Options and Current Strategies" *Stem Cells*, vol. 18, pp. 307-319 (2000).

Lane, B. Josh et al., "Chlamydial Entry Involves TARP Binding of Guanine Nucleotide Exchange Factors", *PLOS Pathogens*, vol. 4, Issue 3 (2008).

Leitinger and Hogg, "The involvement of lipid rafts in the regulation of integrin function", *Journal of Cell Science*, vol. 115, pp. 963-972 (2002).

Melkonian, K., et al., "Role of Lipid Modifications in Targeting Proteins to Detergent-resistant Membrane Rafts", *The Journal of Biological Chemistry*, vol. 274, No. 6, pp. 3910-3917 (1999).

Moffett, S. et al., "Lipid-dependent Targeting of G Proteins into Rafts", *The Journal of Biological Chemistry*, vol. 275, No. 3, pp. 2191-2198 (2000).

Mohan et al., "Characterization of the Epithelial Membrane Protein 2 in the Progression of Endometrial Adenocarcinoma" *Modem Pathology*, Jan. 18 (Supp.1), p. 196A (2005).

Morales, S.A. et al., "Collagen gel contraction by ARPE-19 cells is mediated by a FAK-Src dependent pathway", *Experimental Eye Research*, vol. 85, pp. 790-798 (2007).

MSNBC News Services, "Mixed results on new cancer drug" Nov. 9, pp. 1-4 (2000).

Nichols, B. et al., "Rapid Cycling of Lipid Raft Markers between the Cell Surface and Gogli Complex", *The Journal of Cell Biology*, vol. 153, No. 3, pp. 529-541 (2001).

Niu et al., "Restricted expression pattern of the putative tumor suppressor gene, Epithelial Membrane Protein 2 in the eye" *Invest Ophthalmol Vis. Sci.* E-Abstract 2419 (2002).

Opalinska et al., "Nucleic-Acid Therapeutics: Basic Principles and Recent Applications" *Nature Reviews Drug Discovery*, vol. 1, pp. 503-514 (2002).

Pareek et al., "Detection and Processing of Peripheral Myelin Protein PMP22 in Cultured Schwann Cells" *Journal Biol. Chemistry*, vol. 268, No. 14, pp. 10372-10379 (1993).

(56) References Cited

OTHER PUBLICATIONS

Paul, Ed., "Fv Structure and Diversity in Three Dimensions" *Fundamental Immunology, Third Edition*,. Raven Press, New York, Chapter 8, pp. 292-295 (1993).

Rossi, J.J. et al., "A practical siRNA microbicide?" *Gene Therapy*, vol. 13, pp. 1493-1494 (2006).

Rudikoff et al., "Single amino acid substitution altering antigen-binding specificity" *Proc. Natl. Acad. Sci.*, vol. 79, No. 6, pp. 1979-1983 (1982).

Schubert, S. et al., "Local RNA Target Structure Influences siRNA Efficacy: Systematic Analysis of Intentionally Designed Binding Regions", *J. Mol. Biol.*, vol. 348, pp. 883-893 (2005).

Shimazaki, K. et al., Epithelial membrane protein 2 modulates infectivity of *Chlamydia muridarum* (MoPn), *Microbes and Infection*, vol. 9, pp. 1003-1010 (2007).
Shimazaki K. et al., "Diabodies Targeting Epithelial Membrane Protein 2 Reduce Tumorigencity of Human Endometrial Cancer Cell Lines" *Clin. Cancer Res.,* vol. 14, No. 22, pp. 7367-7377 (2008).
Swanson, K. et al., "*Chlamydia trachomatis* Species-Specific Induction of Ezrin Tyrosine Phosphorylation Functions in Pathogen Entry", *Infection and Immunity*, vol. 75, No. 12, pp. 5669-5677 (2007).
Taylor et al., "Epithelial membrance protein-2 and epithelial membrane protein-3: two novel members of the peripheral myelin protein 22 gene family" *Gene*, vol. 175, pp. 115-120 (1996).
Wadehra, M. et al., "The Tetraspan Protein Epithelial Membrane Protein-2 Interacts with $\beta_1$ Integrins and Regulates Adhesion", *The Journal of Biological Chemistry*, vol. 277, pp. 41094-41100 (2002).
Wadehra, M. et al., "Characterization of the Biology and Pathobiology of Epithelial Membrane Protein-2", University of California Los Angeles Dissertation, ProQuest Information and Learning Company, Ann Arbor Michigan (2002).
Wadehra, M. et al., "Epithelial membrane protein-2 is expressed in discrete anatomical regions of the eye", *Experimental and Molecular Pathology*, vol. 74, Issue 2, pp. 106-112 (2003).
Wadehra, M. et al., "The tetraspan protein EMP2 increases surface expression of class I major histocompatibility complex proteins and susceptibility to CTL-mediated cell death", *Clinical Immunology*, vol. 107, pp. 129-136 (2003).
Wadehra, M. et al., "Epithelial membrane protein-2 regulates surface expression of alphavbeta3 integrin in the endometrium", *Developmental Biology*, vol. 287, Issue 2, pp. 336-345 (2005).
Wadehra, M. et al., "Expression of Epithelial Membrane Protein-2 is Associated with Endometrial Adenocarcinoma of Unfavorable Outcome", *Cancer*, vol. 107(1): pp. 90-98 (2006).

* cited by examiner

SEQUENCE LISTING

```
<160> NUMBER OF SEQ ID NOS: 8

<210> SEQ ID NO 1
<211> LENGTH: 167
<212> TYPE: PRT
<213> ORGANISM: Homo sapiens
<220> FEATURE:
<223> OTHER INFORMATION: human epithelial membrane protein 2 (EMP2, XMP
      protein)

<400> SEQUENCE: 1

Met Leu Val Leu Leu Ala Phe Ile Ile Ala Phe His Ile Thr Ser Ala
  1               5                  10                  15

Ala Leu Leu Phe Ile Ala Thr Val Asp Asn Ala Trp Trp Val Gly Asp
             20                  25                  30

Glu Phe Phe Ala Asp Val Trp Arg Ile Cys Thr Asn Asn Thr Asn Cys
         35                  40                  45

Thr Val Ile Asn Asp Ser Phe Gln Glu Tyr Ser Thr Leu Gln Ala Val
```

```
                50                  55                  60
Gln Ala Thr Met Ile Leu Ser Thr Ile Leu Cys Cys Ile Ala Phe Phe
 65                  70                  75                  80

Ile Phe Val Leu Gln Leu Phe Arg Leu Lys Gln Gly Glu Arg Phe Val
                 85                  90                  95

Leu Thr Ser Ile Ile Gln Leu Met Ser Cys Leu Cys Val Met Ile Ala
            100                 105                 110

Ala Ser Ile Tyr Thr Asp Arg Arg Glu Asp Ile His Asp Lys Asn Ala
            115                 120                 125

Lys Phe Tyr Pro Val Thr Arg Glu Gly Ser Tyr Gly Tyr Ser Tyr Ile
        130                 135                 140

Leu Ala Trp Val Ala Phe Ala Cys Thr Phe Ile Ser Gly Met Met Tyr
145                 150                 155                 160

Leu Ile Leu Arg Lys Arg Lys
                165

<210> SEQ ID NO 2
<211> LENGTH: 20
<212> TYPE: PRT
<213> ORGANISM: Artificial Sequence
<220> FEATURE:
<223> OTHER INFORMATION: Description of Artificial Sequence:20-mer from
      second extracellular loop of human EMP2

<400> SEQUENCE: 2

Glu Asp Ile His Asp Lys Asn Ala Lys Phe Tyr Pro Val Thr Arg Glu
 1               5                  10                  15

Gly Ser Tyr Gly
            20

<210> SEQ ID NO 3
<211> LENGTH: 1484
<212> TYPE: DNA
<213> ORGANISM: Homo sapiens
<220> FEATURE:
<223> OTHER INFORMATION: epithelial membrane protein 2 (EMP2) cDNA
<220> FEATURE:
<221> NAME/KEY: CDS
<222> LOCATION: (195)..(698)
<223> OTHER INFORMATION: EMP2

<400> SEQUENCE: 3
gaggggcccc gccgcctaga gggtggaggg agggcgcgca gtcccagccc agagcttcaa      60
aacagcccgg cggcctcgcc tcgcacccccc agccagtccg tcgatccagc tgccagcgca    120
gccgccagcg ccggcacatc ccgctctggg ctttaaacgt gacccctcgc ctcgactcgc    180
cctgccctgt gaaatgttg gtgcttcttg ctttcatcat cgccttccac atcacctctg    240
cagccttgct gttcattgcc accgtcgaca atgcctggtg ggtaggagat gagtttttttg   300 cagatgtctg gagaatatgt accaacaaca cgaattgcac agtcatcaat gacagctttc    360
aagagtactc cacgctgcag gcggtccagg ccaccatgat cctctccacc attctctgct    420
gcatcgcctt cttcatcttc gtgctccagc tcttccgcct gaagcaggga gagaggtttg    480
tcctaacctc catcatccag ctaatgtcat gtctgtgtgt catgattgcg gcctccattt    540
atacagacag gcgtgaagac attcacgaca aaaacgcgaa attctatccc gtgaccagag    600
aaggcagcta cggctactcc tacatcctgg cgtgggtggc cttcgcctgc accttcatca    660
gcggcatgat gtacctgata ctgaggaagc gcaaatagag ttccggagct gggttgcttc    720
tgctgcagta cagaatccac attcagataa ccatttttgta tataatcatt attttttgag    780
```

-continued

```
gttttctag caaacgtatt gtttcctta aaagccaaaa aaaaaaaaaa aaaaaaaaaa     840
aaaaaaaaaa aaaaaaaaaa aatccaaaag agagaagagt ttttgcattc ttgagatcag    900
agaatagact atgaaggctg gtattcagaa ctgctgccca ctcaaaagtc tcaacaagac    960
acaagcaaaa atccagcaat gctcaaatcc aaaagcactc ggcaggacat ttcttaacca   1020
tggggctgtg atgggaggag aggagaggct gggaaagccg ggtctctggg gacgtgcttc   1080
ctatgggttt cagctggccc aagccccctcc cgaatctctc tgctagtggt gggtggaaga   1140
gggtgaggtg gggtatagga aagaatgac agcttcctga gaggtttcac ccaagttcca     1200
agtgagaagc aggtgtagtc cctggcattc tgtctgtatc caaaccagag cccagccatc   1260
cctccggtat tggggtgggt cagaaaaagt ctcacctcaa tttgccgaca gtgtcacctg    1320
cttgccttag gaatggtcat ccttaacctg cgtgccagat ttagactcgt ctttaggcaa   1380
aacctacagc gcccccccct cacccccagac ctacagaatc agagtcttca agggatgggg   1440
ccagggaatc tgcatttcta atgcgctccc tgggcaacgc ttca                    1484
```

<210> SEQ ID NO 4
<211> LENGTH: 18
<212> TYPE: PRT
<213> ORGANISM: Artificial Sequence
<220> FEATURE:
<223> OTHER INFORMATION: Description of Artificial Sequence:chimeric
      single chain Fv (scFv) V region flexible linker

<400> SEQUENCE: 4

Gly Ser Thr Ser Gly Gly Gly Ser Gly Gly Gly Ser Gly Gly Gly Gly
 1               5                   10                  15

Ser Ser

<210> SEQ ID NO 5
<211> LENGTH: 166
<212> TYPE: PRT
<213> ORGANISM: Mus sp.
<220> FEATURE:
<223> OTHER INFORMATION: mouse epithelial membrane protein 2 (EMP2, XMP
      protein)

<400> SEQUENCE: 5

Met Leu Val Ile Leu Ala Phe Ile Ile Val Phe His Ile Val Ser Thr
 1               5                   10                  15

Ala Phe Ser Thr Ile Asp Asn Ala Trp Thr Val Gly Asp Ser Ala Asp
                20                  25                  30

Leu Arg Val Cys Thr Asn Ser Thr Ala Cys Thr Glu Ile Asn Glu Leu
            35                  40                  45

Thr Gly Pro Glu Ala Phe Glu Gly Tyr Ser Val Trp Gln Ala Val Gln
        50                  55                  60

Ala Thr Met Ile Thr Ile Ile Ser Ser Leu Cys Ile Ser Phe Leu Ile
    65                  70                  75                  80

Phe Leu Leu Gln Leu Phe Arg Leu Lys Gln Gly Glu Arg Phe Val Leu
                85                  90                  95

Thr Ser Ile Ile Gln Leu Met Ser Cys Leu Cys Val Met Ile Gly Ala
            100                 105                 110

Ser Ile Tyr Thr Asp Arg Arg Gln Asp Leu His Gln Gln Ala Arg Lys
        115                 120                 125

Leu Tyr Tyr Leu Leu Gln Glu Gly Ser Tyr Gly Tyr Ser Phe Ile Leu
    130                 135                 140

Ala Trp Val Ala Phe Ala Phe Thr Phe Ile Ser Gly Leu Met Tyr Met
145                 150                 155                 160

```
Ile Leu Arg Lys Arg Lys
            165

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence:EMP2 PCR
      cloning forward primer

<400> SEQUENCE: 6
cgcggatcct ctaccattga caatgcctgg                                      30

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence:EMP2 PCR
      cloning reverse primer

<400> SEQUENCE: 7
ccggaattct tacgcctgca tcacagaata acc                                  33

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence:4 amino acid
      long linker

<400> SEQUENCE: 8

Gly Ser Gly Ser
 1
```

PREVENTION OF CHLAMYDIA INFECTION USING SIRNA

CROSS-REFERENCES TO RELATED APPLICATIONS

This application is a continuation in part claiming priority benefit under 35 U.S.C. §365(c) of International Patent Application Serial No. PCT/US06/014238, filed Apr. 14, 2006, which designated the U.S., and which claims priority benefit of U.S. Patent Application Ser. No. 60/671,755, filed Apr. 15, 2005, the disclosure of each of which is incorporated by reference in its entirety.

STATEMENT AS TO RIGHTS TO INVENTIONS MADE UNDER FEDERALLY SPONSORED RESEARCH AND DEVELOPMENT

This invention was made with Government support under Grant Nos. AI007323, CA009120, CA016042, CA086306, CA119367, GM007185, HD048540 awarded by the National Institutes of Health. The Government has certain rights in this invention. This work was supported by the U.S. Department of Veterans Affairs, and the Federal Government has certain rights in this invention.

REFERENCE TO A "SEQUENCE LISTING," A TABLE, OR A COMPUTER PROGRAM LISTING APPENDIX SUBMITTED ON A COMPACT DISK

Not applicable

FIELD OF THE INVENTION

This invention relates to novel pharmaceutical compositions and methods for treating infection with *Chlamydia*.

BACKGROUND OF THE INVENTION

Chlamydiae are obligate gram-negative intracellular prokaryotic pathogens that are responsible for significant human morbidity and infections of multiple organ systems. More than 90 million new cases of sexually transmitted, genitourinary *Chlamydia trachomatis* infection are reported annually. These infections are a significant cause of infertility, ectopic pregnancy, and chronic pelvic pain syndromes (Brunham, R. C. & Rey-Ladino, *J. Nat Rev Immunol* 5: 149-61 (2005)). Ocular infections with *Chlamydia* may result in trachoma, the primary cause of infectious blindness worldwide (see, Engel, J., *Proc Natl Acad Sci USA* 101: 9947-8 (2004)), and *Chlamydia* species also have been associated with other inflammatory diseases (see, Hannu, T., et al. *Rheumatology* (Oxford) 38: 411-4 (1999), Gencay, M., et al., *Am J Respir Crit Care Med* 163: 1097-100 (2001); Smieja, M., et al., *BMC Infect Dis* 2:21 (2002); and Dautry-Varsat, A., et al., *Traffic* 5: 561-570 (2004)). The pathophysiology of Chlamydial infections is only partly understood, in particular identification of host cellular proteins involved in Chlamydial infection that may reveal new strategies for disease control.

*Chlamydia* has a unique biphasic developmental cycle. The first step in infection requires attachment of a metabolically inactive but infectious, spore-like structure called the elementary body (EB). The initial reversible attachment of EB to epithelial cell layers is proposed to involve a number of Chlamydial and host ligands and adhesions. Possible candidates for attachment mediation include major outer membrane protein (MOMP), heat shock protein 70, OmcB, heparin sulfate-like glycosaminoglycans, polymorphic outer membrane protein gene family (pmp), estrogen receptor complex, and caveolae. Upon cellular attachment local actin polymerization, elicited by intracellular secretion of EB products and tyrosine phosphorylation of various protein species leads to endocytosis of the attached EB. After a few hours, an internalized EB differentiates into the reticulate body (RB), a metabolically active, non-infectious form which gives rise to >1000 progeny EBs, followed by host cell lysis and release of infectious EBs that begin another life cycle (see, Engel, J., *Proc Natl Acad Sci USA* 101, 9947-8 (2004); Dautry-Varsat, A., et al., *Traffic* 5: 561-570 (2004); Gabel, B. R., et al., *Infect Immun* 72: 7367-73 (2004); Davis, V. L., et al., *Proc Natl Acad Sci USA* 99: 9427-32 (2002); Raulston, J. E., et al., (2002) *Infect Immun* 70: 535-43 (2002); Finlay, B. B., et al., *Science* 276: 718-725 (1997); and Virok, D. P., et al., *Infect Immun* 73: 1939-46 (2005)).

Chlamydial infection can result from oral, vaginal, or anal sexual contact with an infected partner. *Chlamydia trachomatis* can be sexually transmitted. In women, the pathogen can cause pelvic inflammatory disease (PID) with a risk of tubal obstruction and infertility. In men, the bacteria can cause epidydimitis and infertility. *Chlamydia* can also cause acute respiratory tract infections in humans. Infection of the eye with *Chlamydia trachomatis*, or trachoma, is a leading cause of preventable blindness worldwide. Chlamydial infections are a particularly serious health threat to newborns who contract occular infections at birth from infected birth canals of their mothers. If untreated, almost 50% of these children develop inclusion conjunctivitis and 20% develop systemic infection resulting in serious pneumonia. *Chlamydia* also is likely to exacerbate atherosclerosis. In particular, coronary heart disease has been associated with increased titers of *Chlamydia* antibodies. In addition, reactive inflammatory arthritis is a common sequel to sexually acquired non-gonococcal genital tract infection. Approximately 50% of reactive inflammatory arthritis cases are associated with *Chlamydia trachomatis* infection of the genital tract. Chlamydial infection can be asymptomatic and irreversible damage may have already occurred before treatment is sought.

Accordingly, *Chlamydia* is a serious public health concern around the world. However, *Chlamydia* is an intracellular pathogen which is difficult to treat. There is no robust vaccine for *Chlamydia* and conventional antibiotic therapies often fail to clear chronic infections.

The epithelial membrane protein-2 (EMP2) is a member of the growth arrest specific-3/peripheral myelin protein-22 (GAS3/PMP22) family of tetraspan proteins. Other four-transmembrane families, connexins and tetraspanins, play roles in gap junctions, cell-cell recognition processes, and intracellular trafficking. Less is known about the GAS3/PMP22 family. The information available mainly relates to their potential roles in various diseases. For instance, mutations in the prototypic GAS3 family member PMP22 have been found to cause neurodegenerative disease (i.e., Dejerrine Sottas Syndrome and Charcot Marie Tooth Syndrome). EMP2 has also been implicated in B cell tumor progression and stress-induced apoptosis.

EMP2 is expressed at high levels in epithelial cells of the lung, eye, and genitourinary tracts. Like several tetraspan proteins (CD9, CD81, PMP22), EMP2 in murine fibroblasts is localized to lipid raft domains. EMP2 controls cell surface trafficking and function of certain integrins, GPI-linked proteins, and class I MHC molecules, and reciprocally regulates caveolin expression. (see, Claas, C., et al., *J Biol Chem* 276: 7974-84 (2001); Hasse, B., et al., *J Neurosci Res* 69: 227-32 (2002); Wadehra, M., et al., *Exp Mol Pathol* 74: 106-12

(2003); Wadehra, M., et al., *Mol Biol Cell* 15: 2073-2083 (2004); Wadehra, M., et al., *J Biol Chem* 277: 41094-41100 (2002); and Wadehra, M., et al., *Clin Immunol* 107: 129-136 (2003)).

Detailed studies of the subanatomic distribution of EMP2 in murine and human ocular tissue indicate that EMP2 is localized to epithelial layers of the cornea, ciliary body, and retinal pigmented epithelium-choroid, the stromal layers of the sclera, and the nerve fiber layer of the retina and optic nerve. This distribution is distinct from other TM4SF proteins and may relate to a role in apical membrane recycling.

Recent studies indicate that the interaction between *Chlamydia* and host cells occurs at specific cholesterol- and glycosphingolipids-rich lipid raft microdomains. Lipid rafts, often experimentally defined by their insolubility in cold non-ionic detergents are believed to be subspecialized cell membrane regions important in assembly of receptor signaling complexes, protein trafficking, endocytic and secretory pathways. Many other proteins associated with bacterial infection have been found in lipid raft compartments. Dautry-Varsat, A., et al., *Traffic* 5: 561-570 (2004); Simons, K., et al., *Nature* 387: 569-572 (1997); Gabel, B. R., et al., *Infect Immun* 72: 7367-73 (2004); Claas, C., et al., J Biol Chem 276, 7974-84 (2001); Brown, D. A., et al. *J Biol Chem* 275: 17221-4 (2000); and Subtil, A., et al., *J Cell Sci* 117: 3923-33 (2004); and Webley, W. C., et al., *BMC Infect Dis* 4: 23 (2004)

As reported herein, the Applicants have now surprisingly discovered that EMP2 is a molecular cell entry point for *Chlamydia* and that EMP2 polypeptides, anti-EMP2 antibodies, and EMP2 siRNA can modulate the ability of *Chlamydia* to enter a host cell to cause infection and disease. As discussed above, there remains a large need for methods and compositions which are useful in the prevention, treatment, and modulation of *Chlamydia* infection. Accordingly, this invention provides novel compositions and methods for meeting these and other needs.

BRIEF SUMMARY OF THE INVENTION

In its various aspects, the invention relates to the discovery that epithelial membrane protein-2 (EMP2) is a molecular cell entry point for *Chlamydia* and that inhibiting the access of *Chlamydia* to EMP2 can inhibit the ability of *Chlamydia* to enter a host cell and/or to cause infection. Accordingly, in a first aspect, the invention provides pharmaceutical compositions comprising EMP2 *Chlamydia* inhibitors and methods of using them in the prevention or treatment of infection with *Chlamydia* or the entry of *Chlamydia* into a host cell expressing EMP2.

In this first aspect, the invention provides pharmaceutical compositions of EMP2 polypeptides. In some embodiments, the EMP2 polypeptides can be the full EMP2 polypeptide of SEQ ID NO:1 or a fragment thereof which is capable of binding to an EMP2 antibody and/or which blocks the infectivity of *Chlamydia*. The EMP2 polypeptide can also be a fragment of the EMP2 polypeptide of SEQ ID NO:1 which is capable of antagonizing the ability of the EMP2 antibody to inhibit or block the entry of *Chlamydia* into a host cell bearing the EMP2 polypeptide on the cell surface. The EMP2 polypeptide can also be a fragment of the EMP2 polypeptide which is capable of inhibiting or blocking the entry of *Chlamydia* into the host cell. In still further embodiments of any of the above, the EMP2 polypeptide comprises, consists essentially of, or consists of the extracellular loop polypeptide of EMP2 or the amino polypeptide having the amino acid sequence of SEQ ID NO:2. In still further embodiments of the above, the EMP2 polypeptide can be a variant of the EMP2 polypeptide of SEQ ID NO:1 or SEQ ID NO:2.

In other embodiments of this first aspect, the invention provides pharmaceutical compositions comprising an anti-EMP2 antibody which is capable of specifically binding to the EMP2 of a host cell and of inhibiting the ability of *Chlamydia* to enter the host cell or infect a host. The anti-EMP2 antibody may attach to any epitope of the EMP polypeptide. In some embodiments the antibody can bind to a polypeptide comprising the amino acid sequence of SEQ ID NO: 1 or SEQ ID NO:2. In some embodiments, the antibody recognizes an extracellular or external epitope (e.g., external loop antigen) of EMP2. In any of the above embodiments, the anti-EMP2 antibody can be a polyclonal antibody or a monoclonal antibody. In addition, the antibody may further be a human antibody, a humanized antibody, a chimeric antibody, a recombinant antibody, or an antibody fragment.

In this first aspect, the invention also provides a pharmaceutical composition comprising an EMP2 siRNA molecule and/or an siRNA expression vector which comprise a nucleotide sequence complementary to that of SEQ ID NO:3. In some embodiments, the EMP2 siRNA has substantial or complete identity to that of SEQ ID NO:3 and forms a double stranded siRNA. In further embodiments, the EMP2 siRNA is at least about 15-50 nucleotides in length (e.g., each complementary sequence of the double stranded siRNA is 15-50 nucleotides in length, and the double stranded siRNA is about 15-50 base pairs in length). In some further embodiments still, the length of the EMP2 siRNA molecule is about 20-30 base nucleotides, about 20-25 or about 24-29 nucleotides in length, e.g., 20, 21, 22, 23, 24, 25, 26, 27, 28, 29, or 30 nucleotides in length. In still further embodiments, the EMP2 siRNA is a hairpin loop siRNA.

In this first aspect the invention also provides pharmaceutical compositions comprising an EMP2 ribozyme which is capable of inhibiting the expression of EMP2 in a host cell transduced with the EMP2 ribozyme.

In this first aspect, the invention also accordingly provides for the use of a EMP2 *Chlamydia* inhibitor (e.g., the above described EMP2 polypeptides, anti-EMP2 antibodies, or EMP2 siRNAs, and EMP2 ribozymes) in the manufacture of a medicament for treating *chamydia*. In this aspect, the invention also provides pharmaceutical compositions comprising the above-described EMP2 polypeptides, anti-EMP2 antibodies, and EMP2 siRNA for the treatment or prevention of *Chlamydia* infections.

In some embodiments, the above described pharmaceutical compositions which comprise the EMP2 *Chlamydia* inhibitor (e.g., an anti-EMP2 antibody, EMP2 polypeptide, EMP2 siRNA, or EMP2 ribozyme) are formulated for topical application to the surface of the eye or a mucosal surface. In some additional embodiments of the above, the pharmaceutical compositions are formulated as part of an antibiotic composition which may be a cream, lotion, gel or ointment. These antibiotics include, but are not limited to, azithromycin, amoxicillin, doxycycline, erythromycin, erythromycin ethylsuccinate, ofloxacin and levofloxacin. In some further embodiments, the pharmaceutical compositions according to the invention are formulated as part of a contraceptive composition which may be a cream, lotion, ointment, or gel comprising a spermicidal agent. In still other embodiments, the pharmaceutical compositions of the invention are formulated with a lubricant. In some embodiments, the EMP2 *Chlamydia* inhibitor is formulated as an intravaginal or condom-coating medicament including, but not limited to, ointments, lotions, gels, and creams.

In still other embodiments of the above pharmaceutical compositions which comprise an EMP2 polypeptide or anti-EMP2 antibody, the compositions are formulated for topical administration to the eye. These compositions may be co-formulated with an antibiotic useful in treating *Chlamydia* infection.

In a second aspect, the invention also provides methods of treating *Chlamydia* infections using the above-described pharmaceutical compositions. In this first aspect, the invention also provides methods for treating or preventing infection with *Chlamydia* in a subject by administering a pharmaceutical composition comprising a therapeutically effective amount of an EMP2 *Chlamydia* inhibitor (e.g., EMP2 polypeptide, anti-EMP2 antibody, EMP2 ribozyme or EMP2 siRNA) to the subject. In some embodiments, the person to be treated has been diagnosed as having a *Chlamydia* infection or has or will engage in behavior which places them at risk for such infection. In some embodiments, the *Chlamydia* species is *C. trachoma*. In some embodiments, the subject is a person who is infected with *Chlamydia* and has been diagnosed with conjunctivitis, pelvic inflammatory disease, arteriosclerosis, elevated C-reactive protein, arthritis, a urogenital tract infection or pneumonia exacerbated or associated with infection by *Chlamydia*. In some embodiments, the subject is also treating with an antibiotic useful in treating *Chlamydia* infections. These antibiotics include, but are not limited to, azithromycin, amoxicillin, doxycycline, erythromycin, erythromycin ethylsuccinate, ofloxacin and levofloxacin.

In a third aspect, the invention provides compositions of EMP2 *Chlamydia* inhibitors (e.g., EMP2 polypeptides, anti-EMP2 antibodies, EMP2 siRNA, and EMP2 ribozymes) which can be used to inhibit or prevent the entry of *Chlamydia* into a host cell which expresses EMP2 or is otherwise is capable of expressing EMP2.

In this third aspect, in some embodiments, the entry of *Chlamydia* into the host cell is inhibited by contacting the host cell with an anti-EMP2 antibody, an EMP2 siRNA or an EMP2 ribozyme. In other embodiments, the entry is inhibited by contacting the *Chlamydia* with an EMP2 polypeptide. The EMP2 *Chlamydia* inhibitors may be formulated in a physiologically acceptable carrier, preferably, sterile.

In fourth aspect, the invention provides methods of identifying EMP2 *Chlamydia* inhibitors (e.g., EMP2 polypeptides, anti-EMP2 antibodies, and EMP2 siRNA) which would be of use in treating or preventing infection with *Chlamydia*. In some embodiments, a host cell which expresses EMP2 is contacted with the candidate agent and the effect of the agent on the ability of *Chlamydia* to enter or bind to the host cell is determined. In some embodiments, the host cell is a recombinant host cell which has been transduced with, and expresses, a gene encoding EMP2. In some embodiments, the candidate EMP2 polypeptide is contacted with an anti-EMP2 antibody which is capable of inhibiting the ability of *Chlamydia* to bind or enter a host cell expressing EMP2 and the ability of the EMP2 polypeptide to inhibit the binding of EMP2 to the antibody is determined.

In each of the above embodiments, the host cell or subject to be treated can be human, primate, or mammal (e.g., mouse, rat, rabbit) or bird. In further embodiments of any of the above aspects, the *Chlamydia* is *C. trachoma*.

DETAILED DESCRIPTION

Figure 1:
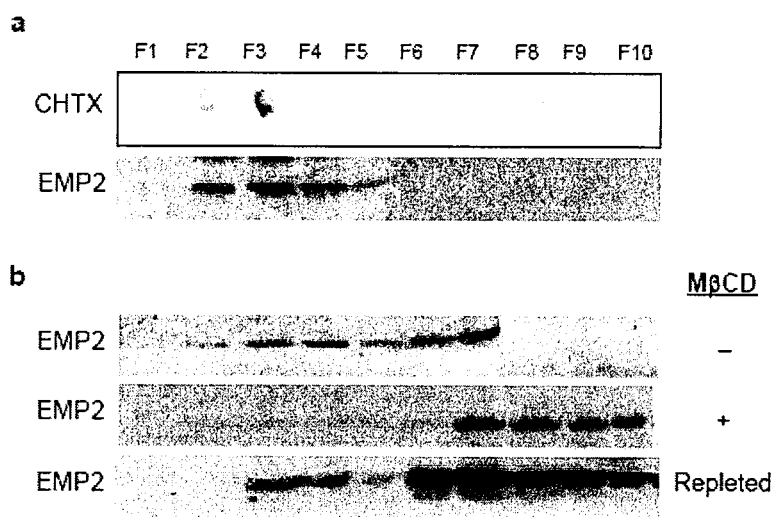
FIG. 1 illustrates that EMP2 is targeted to lipid rafts and is disrupted following MβCD treatment. (a, b) Lipid raft fractionation by Brij 58 insolubility. HEC1A were lysed in 1% Brij 58, and centrifuged in a sucrose density gradient. Ten fractions (400 μl each) were collected from the gradient top and tested for (a) GM1 ganglioside by cholera toxin dot blot and (b) EMP2 (~$M_r$ 20 kDa) using SDS-PAGE and western analysis. (c) Cholesterol dependence of EMP2 lipid raft fractionation. HEC1A cells were preincubated in the absence (−) or presence (+) of MPCB, or repleted with cholesterol after MPCB treatment. Cells were then lysed in 1% Triton X-100, gradient fractionated, and EMP2 detected by western analysis. Experiments were performed independently three times with similar results.

Chlamydiae are bacterial pathogens which have evolved efficient strategies to enter, replicate, and persist inside host epithelial cells, resulting in acute and chronic diseases of humans and other animals. Understanding the molecular basis of initial Chlamydial attachment and entry is necessary to form strategies for prevention and treatment. However, few molecules of either Chlamydial or host origin have emerged as candidates for these processes, and the precise mechanism of infection has not been elucidated. Epithelial membrane protein-2 (EMP2) is a 4-transmembrane protein, highly expressed in epithelial cells of common sites for Chlamydial infection.

The Applicants have discovered that EMP2 resides in lipid rafts and is the target membrane microdomain for Chlamydial infection. They have also found that Chlamydial attachment and infection efficiency is linked to levels of EMP2 expression in HEC1A endometrial cells. Either blocking surface EMP2 with anti-EMP2 antibody or recombinant knockdown in EMP2 expression reduced both Chlamydial attachment and infection efficiency, whereas these processes were markedly augmented when EMP2 was recombinantly overexpressed. These findings indicate that EMP2 is a new host protein involved in *Chlamydia* attachment and infection.

Accordingly, the invention provides compositions of EMP2 *Chlamydia* inhibitors in a physiologically acceptable carrier or a pharmaceutically acceptable carrier and methods of treating *Chlamydia* infections or preventing the entry of *Chlamydia* into a host cell using the EMP2 *Chlamydia* inhibitors.

DEFINITIONS

Unless otherwise stated, the following terms used in the specification and claims have the meanings given below.

It is noted here that as used in this specification and the appended claims, the singular forms "a," "an," and "the" include plural reference unless the context clearly dictates otherwise.

Chlamydiae are obligate intracellular bacteria that infect animals, including mammals and birds, particularly at the epithelial lining of the lung, conjunctivae or genital tract. The term "*Chlamydia*" references the most common species of *Chlamydia* (i.e., *Chlamydia trachomatis, Chlamydia psittaci, Chlamydia pecorum* and *Chlamydia pneumoniae*). Recently, the newly designated species of *Chlamydia, C. pneumoniae* (formerly *C. trachomatis* TWAR) has been implicated as a major cause of epidemic human pneumonitis and perhaps may play a role in atherosclerosis.

"Inhibitors" are agents that inhibit a recited activity, function or entity. For example an inhibitor of *Chlamydia* infection blocks or reduces the ability of a *Chlamydia* bacteria to cause an infection. An inhibitor of *Chlamydia* entry into a host cell is an agent which blocks, prevents, decreases, reduces, or delays the entry of the bacteria into the host cell. An inhibitor of EMP2 binding to an anti-EMP2 antibody is an agent which reduces or competes with the binding of the EMP2 to the anti-EMP2 antibody.

An "EMP2 *Chlamydia* inhibitor" is an agent which interferes with the ability of *Chlamydia* to infect a host cell by interfering with *Chlamydia*'s ability to interact with, or bind to, EMP2 of the host cell. A EMP2 *Chlamydia* inhibitor can be EMP2 polypeptide; an anti-EMP2 antibody; an EMP2 siRNA molecule; an EMP2-ribozyme; a compound which competes with binding of *Chlamydia* to EMP2, or an agent or compound which inhibits the expression, transcription, or translation of EMP2 nucleic acids in a host cell. In some embodiments, the EMP2 *Chlamydia* inhibitors are provided in a composition also comprising a sterile carrier and/or physiologically acceptable carrier.

A "host cell" is a living cell which is capable of being infected with *Chlamydia* and expresses EMP2. Exemplary host cells are mammalian epithelial cells, including epithelial cells of the mucosa or eye. The host cells may be in vivo or in vitro.

Modulators are agents which can increase or decrease a referenced activity. Modulators include inhibitors and activators which have effects opposite to inhibitors (e.g., increase, stimulate, augment, enhance, accelerate) a referenced activity or entity.

An EMP2 polypeptide according to the invention comprises a polypeptide which inhibits, partially or totally blocks, decreases, prevents, delays, or reduces the ability of *Chlamydia* to enter a host cell or cause infection. In some embodiments, an EMP2 polypeptide according to the invention can prevent, or compete with, the binding of EMP2 to an anti-EMP2-antibody which recognizes EMP2 and that can interfere with the ability of *Chlamydia* to enter a host cell or cause invention. In some embodiments, an EMP2 polypeptide according to the invention can prevent or reduce the ability of a *Chlamydia* to enter a host cell expressing EMP2 by competing with the host cells' EMP2 for binding to *Chlamydia*.

With regard to amino acid sequence, an EMP2 polypeptide according to the invention 1) comprises, consists of, or consists essentially of an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of over a region of at least about 15, 20, 25, 50, 75, 100, 125, 150 or more amino acids, to a polypeptide of SEQ ID NO: 1 and 2) can either specifically bind to an antibody, e.g., polyclonal antibody, raised against an epitope of EMP2 or inhibit the ability of *Chlamydia* to enter a host cell expressing the EMP2 polypeptide of SEQ ID NO: 1 or inhibit the infectivity of *Chlamydia*. In some embodiments, the EMP2 polypeptide is a fragment comprising, consisting of, or consisting essentially of the sequence of EMP2 from position 16 to 64, 20 to 60, 20 to 50, 20 to 40, or 30 to 64 or 40 to 64 of SEQ ID NO: 1. In some embodiments, the EMP2 polypeptide is a fragment comprising, consisting of, or consisting essentially of the sequence of EMP2 from position 60 to 100, 80 to 150, 100 to 150, 110 to 140, 120 to 140, 50 to 150, or 100 to 160 of SEQ ID NO: 1. In some embodiments, the EMP2 fragment comprises an epitope recognized by an anti-EMP2 antibody which inhibits the ability of *Chlamydia* to enter or bind a host cell expressing EMP2. In some embodiments of any of the above, the EMP2 fragment may be from 15 to 25, 15 to 40, 25 to 50, 50 to 100 amino acids long, or longer.

An EMP2 polypeptide according to the invention may be a conservatively modified variant of a polypeptide of SEQ ID NO: 1. Accordingly, in some embodiments of the above, the EMP polypeptide consists of the sequence of EMP2 of SEQ ID NO: 1 or a fragment thereof. The fragment may be from 15 to 25, 15 to 40, 25 to 50, 50 to 100 amino acids long, or longer. The fragment may correspond to that of EMP2 from position 16 to 64 of SEQ ID NO: 1. In other embodiments, the EMP2 polypeptide or fragment comprises a sequence of EMP2 of SEQ ID NO: 1 or SEQ ID NO:2 having from 1, 2, 3, 4, or 5 conservative amino acid modifications or 1, 2, 3, 4, or 5 substitutions with a artificial chemical mimetic of the corresponding naturally occurring amino acid. The fragment may be from 15 to 25, 15 to 40, 25 to 50, 50 to 100 amino acids long, or longer. In some other embodiments still, the EMP2 polypeptide sequence can be that of a mammal including, but not limited to, primate, e.g., human; rodent, e.g., rat, mouse, hamster; cow, pig, horse, sheep. The proteins of the invention include both naturally occurring or recombinant molecules. In some embodiments, the amino acids of the EMP2 polypeptide are all naturally occurring amino acids as set forth below. In other embodiments, one or more amino acids may be substituted by an artificial chemical mimetic of a corresponding naturally occurring amino acids.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Methods for obtaining (e.g., producing, isolating, purifying, synthesizing, and recombinantly manufacturing) polypeptides are well known to one of ordinary skill in the art.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

As to "conservatively modified variants" of amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

An "anti-EMP2 antibody" or "EMP2 antibody" according to the invention is an antibody which can bind to the EMP2 polypeptide of SEQ ID NO: 1. The antibodies according to the invention can act to inhibit the ability of *Chlamydia* to enter a host cell or cause infection. Without being wed to theory, it is believed that the antibodies act to inhibit the ability of *Chlamydia* to enter the host cell or cause an infection by reducing the availability of the host's endogenous EMP2 for interacting or binding with *Chlamydia*. The antibodies for use according to the invention include, but are not limited to, recombinant antibodies, polyclonal antibodies, monoclonal antibodies, chimeric antibodies, human monoclonal antibodies, humanized or primatized monoclonal antibodies, and antibody fragments. The antibodies preferably bind to an external loop sequence of EMP2. In some embodiments, the antibodies bind to a polypeptide having the sequence of SEQ ID NO:2.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

Accordingly, the term antibody also embraces minibodies, diabodies, triabodies and the like. Diabodies are small bivalent biospecific antibody fragments with high avidity and specificity. Their high signal to noise ratio is typically better due to a better specificity and fast blood clearance increasing their potential for diagnostic and therapeutic targeting of specific antigen (Sundaresan et al., *J Nucl Med* 44:1962-9 (2003). In addition, these antibodies are advantageous because they can be engineered if necessary as different types of antibody fragments ranging from a small single chain Fv to an intact IgG with varying isoforms (Wu & Senter, *Nat. Biotechnol.* 23:1137-1146 (2005)). In some embodiments, the antibody fragment is part of a diabody. Exemplary diabodies for use according to the invention include those designated herein as KS41, KS49, KS83, KS89.

For preparation of antibodies, e.g., recombinant, monoclonal, or polyclonal antibodies, many techniques known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* ($3^{rd}$ ed. 1997)). Techniques for the production of single chain antibodies or recombinant antibodies (U.S. Pat. No. 4,946,778, U.S. Pat. No. 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121: 210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., *Nature* 321:522-525 (1986); Riechmann et al., *Nature* 332: 323-327 (1988); Verhoeyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only those polyclonal antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Using Antibodies, A Laboratory Manual* (1998) for a description of immunoassay formats and conditions that can be used to determine specific immunoreactivity).

For example, rabbit polyclonal antibodies to EMP2 are known in the art (see, Wang, C. X., et al. Blood 97, 3890-3895 (2001)). Such antibodies may be obtained using glutathione-S-transferase-EMP2 fusion proteins. Rabbit antibodies can be generated against the first extracellular region of the gene (from amino acid 16 to 64) constructed as a glutathione-S-transferase (GST)-EMP2 fusion protein. The EMP2 peptide can be cloned by PCR using the following primers: CGC GGATCCTCTACCATTGACAATGCCTGG (forward; BamHI underlined; SEQ ID NO:6); CCG GAATTCTTACGCCTGCATCACAGAATAACC (reverse, EcoRI underlined; SEQ ID NO:7). The PCR product can be directionally cloned into the BamHI and EcoRI sites of the pGEX-4T-1 vector that contains GST gene (Pharmacia). The EMP2 fragment is cloned in frame with the GST to create a fusion protein. The insert can be confirmed by sequencing. The GST fusion protein can be produced as previously described (see, Smith D B et al., Gene 67:31-40 (1988)). Bacteria in log phase ($OD_{600}$ 0.6 to 0.9) can be induced for 2.5 to 3 hours at 37° C. with 1 mM isopropyl-1-thio-β-D-galactopyranoside. Bacteria are lysed, and the soluble fraction loaded onto a glutathione-Sepharose column (Pierce, Rockford, Ill.). The columns are washed with 10 bed volumes of phosphate-buffered saline (PBS)/EDTA. The fusion protein elutes from the column using 20 mM reduced glutathione (Sigma, St Louis, Mo.) in 50 mM Tris-Cl, pH 8.0. For antibody preparation, rabbits are immunized twice with the GST-EMP2 fusion protein, and serum is collected, starting 2 weeks after the last immunization (Research Genetics, Huntsville, Ala.).

Example 6 exemplifies an approach for obtaining fully human monoclonal antibodies to EMP2. These antibodies can be produced using recombinant phage-display technology from a human antibody phage-display gene library. Such monoclonal antibodies to human EMP2 can be used for diagnostic purposes, and as EMP2 Chlamydial inhibitors for prevention or treatment of *Chlamydia* infection. Monoclonal antibodies to mouse EMP2 can be similarly prepared for use in validating the therapeutic strategy in pre-clinical mouse models of *Chlamydia* infection in vivo.

In some embodiments, the invention provides an "EMP2 siRNA" for use in preventing, treating or inhibiting a *Chlamydia* infection. In this embodiment, the siRNA has a sequence which is complementary to that of SEQ ID NO:3 and is capable of reducing the expression of EMP2 in a target cell of the host.

An "siRNA" or "RNAi" refers to a nucleic acid that forms a double stranded RNA, which double stranded RNA has the ability to reduce or inhibit expression of a gene or target gene when the siRNA expressed in the same cell as the gene or target gene. "siRNA" or "RNAi" thus refers to the double stranded RNA formed by the complementary strands. The complementary portions of the siRNA that hybridize to form the double stranded molecule typically have substantial or complete identity. In one embodiment, an siRNA refers to a nucleic acid that has substantial or complete identity to a target gene and forms a double stranded siRNA. Typically, the siRNA is at least about 15-50 nucleotides in length (e.g., each complementary sequence of the double stranded siRNA is 15-50 nucleotides in length, and the double stranded siRNA is about 15-50 base pairs in length, preferable about preferably about 20-30 base nucleotides, preferably about 20-25 or about 24-29 nucleotides in length, e.g., 20, 21, 22, 23, 24, 25, 26, 27, 28, 29, or 30 nucleotides in length.

The design and making of siRNA molecules and vectors are well known to those of ordinary skill in the art. For instance, an efficient process for designing a suitable siRNA is to start at the AUG start codon of the mRNA transcript (e.g., see, FIG. 5) and scan for AA dinucleotide sequences (see, Elbashir et al. EMBO J 20: 6877-6888 (2001). Each AA and the 3' adjacent nucleotides are potential siRNA target sites. The length of the adjacent site sequence will determine the length of the siRNA. For instance, 19 adjacent sites would give a 21 Nucleotide long siRNA siRNAs with 3' overhanging UU dinucleotides are often the most effective. This approach is also compatible with using RNA pol III to transcribe hairpin siRNAs. RNA pol III terminates transcription at 4-6 nucleotide poly(T) tracts to create RNA molecules having a short poly(U) tail. However, siRNAs with other 3' terminal dinucleotide overhangs can also effectively induce RNAi and the sequence may be empirically selected. For selectivity, target sequences with more than 16-17 contiguous base pairs of homology to other coding sequences can be avoided by conducting a BLAST search (see, www.ncbi.nlm.nih.gov/BLAST).

The siRNA can be administered directly or an siRNA expression vectors can be used to induce RNAi. A vector can have inserted two inverted repeats separated by a short spacer sequence and ending with a string of T's which serve to terminate transcription. The expressed RNA transcript is predicted to fold into a short hairpin siRNA. The selection of siRNA target sequence, the length of the inverted repeats that encode the stem of a putative hairpin, the order of the inverted repeats, the length and composition of the spacer sequence that encodes the loop of the hairpin, and the presence or absence of 5'-overhangs, can vary. A preferred order of the siRNA expression cassette is sense strand, short spacer, and antisense strand. Hairpin siRNAs with these various stem lengths (e.g., 15 to 30) are suitable. The length of the loops linking sense and antisense strands of the hairpin siRNA can have varying lengths (e.g., 3 to 9 nucleotides, or longer). The vectors may contain promoters and expression enhancers or other regulatory elements which are operably linked to the nucleotide sequence encoding the siRNA.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers. These control elements may be designed to allow the clinician to turn off or on the expression of the gene by adding or controlling external factors to which the regulatory elements are responsive.

In some embodiments, the EMP2 *Chlamydia* inhibitor is an EMP2 ribozyme which can inhibit the expression of EMP2 when present in a cell. Ribozymes are enzymatic RNA molecules capable of catalysing the specific cleavage of RNA. The mechanism of ribozyme action involves sequence specific hybridisation of the ribozyme molecule to complementary target RNA, followed by an endonucleolytic cleavage. Within the scope of the invention are engineered hammerhead motif ribozyme molecules that specifically and efficiently catalyse endonucleolytic cleavage of EMP2 mRNA, including particularly the mRNA of SEQ ID NO:3. Specific ribozyme cleavage sites within any potential RNA target are initially identified by scanning the target molecule for ribozyme cleavage sites, which include the following sequences, GUA, GUU and GUC. Once identified, short RNA sequences of between 15 and 20 ribonucleotides corresponding to the region of the target gene containing the cleavage site may be evaluated for predicted structural features such as secondary structure that may render the oligonucleotide sequence unsuitable. Both anti-sense RNA and DNA molecules and ribozymes of the invention may be prepared by any method known in the art for the synthesis of RNA molecules. These include techniques for chemically synthesizing oligodeoxyribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors, which incorporate suitable RNA polymerase promoters such as the T7 or SP6 polymerase promoters. Methods of making ribozymes are well known in the art (see, for instance, U.S. Patent Application Publication No. 20060062785).

Construction of suitable vectors for the EMP2 siRNA or EMP2 Ribozymes containing the desired EMP2 siRNA or EMP2 Ribozyme sequences and control sequences employs standard ligation and restriction techniques, which are well understood in the art (see Maniatis et al., in Molecular Cloning: A Laboratory Manual, Cold Spring Harbor Laboratory, New York (1982)). Isolated plasmids, DNA sequences, or synthesized oligonucleotides are cleaved, tailored, and religated in the form desired.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

The terms "identical" or percent "identity," in the context of two or more nucleic acids or polypeptide sequences, including EMP2 siRNA and EMP2 polypeptides, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection. Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to the full length of the reference sequence, usually about 25 to 100, or 50 to about 150, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. An example of potassium channel splice variants is discussed in Leicher, et al., *J. Biol. Chem.* 273(52):35095-35101 (1998).

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al., John Wiley & Sons.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. N.Y.).

The EMP2 antibody or EMP2 polypeptide according to the invention can have a label or detectable moiety attached thereto. A "label" or a "detectable moiety" is a composition detectable by spectroscopic, photochemical, biochemical, immunochemical, chemical, or other physical means. For example, useful labels include $^{32}$P, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "test compound" or "candidate molecule" or "modulator" or grammatical equivalents as used herein describes any molecule, either naturally occurring or synthetic, e.g., protein, polypeptide, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, lipid, fatty acid, polynucleotide, RNAi, oligonucleotide, etc. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 Daltons and less than about 2500 Daltons, preferably less than about 2000 Daltons, preferably between about 100 to about 1000 Daltons, more preferably between about 200 to about 500 Daltons.

"Determining the functional effect" refers to assaying for a compound that increases or decreases a parameter that is indirectly or directly under the influence of a polynucleotide or polypeptide for use according to the invention, e.g., measuring physical and chemical or phenotypic effects. Such functional effects can be measured by any means known to those skilled in the art, e.g., changes in spectroscopic (e.g., fluorescence, absorbance, refractive index), hydrodynamic (e.g., shape), chromatographic, or solubility properties for the protein; measuring inducible markers or transcriptional activation of the protein; measuring binding activity or binding assays, e.g. binding to antibodies; measuring changes in ligand binding affinity; e.g., via chemiluminescence, fluorescence, colorimetric reactions, antibody binding, inducible markers, and ligand binding assays.

Samples or assays for identifying a EMP2 *Chlamydia* inhibitor of the invention are conducted in the presence of the candidate inhibitor and then the results are compared to control samples without the inhibitor to examine for the desired activity or to determine the functional effect of the candidate inhibitor. A positive reference control which is an agent having the desired activity may be used. In the case of EMP2 polypeptides, the positive control agent may be EMP2 itself. Control samples (untreated with inhibitors) are assigned a relative of 100%. Inhibition is achieved when the activity value relative to the control is about 80%, preferably 50%, more preferably 25 to 0%. Suitable methods for identifying inhibitors for use according to the invention are set forth in the Examples.

Compositions.

When used for pharmaceutical purposes, the EMP2 *Chlamydia* inhibitors used according to the invention are typically formulated in a suitable buffer, which can be any pharmaceutically acceptable buffer, such as phosphate buffered saline or sodium phosphate/sodium sulfate, Tris buffer, glycine buffer, sterile water, and other buffers known to the ordinarily skilled artisan such as those described by Good et al. *Biochemistry* 5:467 (1966). The compositions can additionally include a stabilizer, enhancer, or other pharmaceutically acceptable carriers or vehicles. A pharmaceutically acceptable carrier can contain a physiologically acceptable compound that acts, for example, to stabilize the nucleic acids or polypeptides of the invention and any associated vector. A physiologically acceptable compound can include, for example, carbohydrates, such as glucose, sucrose or dextrans; antioxidants, such as ascorbic acid or glutathione; chelating agents; low molecular weight proteins or other stabilizers or excipients. Other physiologically acceptable compounds include wetting agents, emulsifying agents, dispersing agents, or preservatives, which are particularly useful for preventing the growth or action of microorganisms. Various preservatives are well known and include, for example, phenol and ascorbic acid. Examples of carriers, stabilizers, or adjuvants can be found in Remington's *Pharmaceutical Sciences*, Mack Publishing Company, Philadelphia, Pa., 17th ed. (1985).

The pharmaceutical compositions according to the invention comprise a therapeutically effective amount of a EMP2 *Chlamydia* inhibitor (e.g., EMP2-polypeptide, anti-EMP2 antibody, EMP2 si RNA, or EMP2 ribozyme) according to the invention and a pharmaceutically acceptable carrier. By "therapeutically effective dose or amount" herein is meant a dose that produces effects for which it is administered (e.g., treatment or prevention of a *Chlamydia* infection). The exact dose and formulation will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); *Remington. The Science and Practice of Pharmacy*, 20th Edition, Gennaro, Editor (2003), and Pickar, *Dosage Calculations* (1999)). The EMP2 *Chlamydia* inhibitor, if a salt, is formulated as a "pharmaceutically acceptable salt."

A "pharmaceutically acceptable salt" or to include salts of the active compounds which are prepared with relatively nontoxic acids or bases, according to the route of administration. When inhibitors of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Aside from biopolymers such as nucleic acids and polypeptides, certain compounds of the present invention possess asymmetric carbon atoms (optical centers) or double bonds; the racemates, diastereomers, geometric isomers and individual isomers are all intended to be encompassed within the scope of the present invention. In preferred embodiments, wherein the compound comprises amino acids or nucleic acids, the amino acids and nucleic acids are each the predominant naturally occurring biological enantiomer.

The compositions for administration will commonly comprise an agent as described herein dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs.

Suitable formulations for use in the present invention are found in *Remington: The Science and Practice of Pharmacy*, 20th Edition, Gennaro, Editor (2003) which is incorporated herein by reference. Moreover, for a brief review of methods for drug delivery, see, Langer, *Science* (1990) 249:1527-1533, which is incorporated herein by reference. The pharmaceutical compositions described herein can be manufactured in a manner that is known to those of skill in the art, i.e., by means of conventional mixing, dissolving, granulating, dragee-making, levigating, emulsifying, encapsulating, entrapping or lyophilizing processes. The following methods and excipients are merely exemplary and are in no way limiting.

For injection, the compounds of the present invention can be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the inhibitors for use according to the invention can be formulated readily by combining with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, such as the cross-linked polyvinyl pyrrolidone, agar, or alginic acid or a salt thereof such as sodium alginate.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

In some embodiments, a pharmaceutical composition for intravenous administration may provide from about 0.1 to 100 mg per patient per day. Dosages from 0.1 up to about 100 mg per patient per day may be used. Substantially higher dosages are possible in topical administration. Actual methods for preparing parenterally administrable compositions will be known or apparent to those skilled in the art and are described in more detail in such publications as *Remington: The Science and Practice of Pharmacy,* 21st Edition 2005, Lippincott Williams & Wilkins, Publishers.

The pharmaceutical compositions can be administered in a variety of dosage forms and amounts depending upon the method of administration. For example, unit dosage forms suitable for oral administration include, but are not limited to, powder, tablets, pills, capsules and lozenges. It is recognized that antibodies when administered orally, should be protected from digestion. This is typically accomplished either by complexing the molecules with a composition to render them resistant to acidic and enzymatic hydrolysis, or by packaging the molecules in an appropriately resistant carrier, such as a liposome or a protection barrier. Means of protecting agents from digestion are well known in the art.

Pharmaceutical formulations, particularly, of the polypeptide and nucleic acid EMP2 *Chlamydia* inhibitors for according to the present invention can be prepared by mixing an antibody having the desired degree of purity with optional pharmaceutically acceptable carriers, excipients or stabilizers. Such formulations can be lyophilized formulations or aqueous solutions. Acceptable carriers, excipients, or stabilizers are nontoxic to recipients at the dosages and concentrations used. Acceptable carriers, excipients or stabilizers can be acetate, phosphate, citrate, and other organic acids; antioxidants (e.g., ascorbic acid) preservatives low molecular weight polypeptides; proteins, such as serum albumin or gelatin, or hydrophilic polymers such as polyvinylpyllolidone; and amino acids, monosaccharides, disaccharides, and other carbohydrates including glucose, mannose, or dextrins; chelating agents; and ionic and non-ionic surfactants (e.g., polysorbate); salt-forming counter-ions such as sodium; metal complexes (e.g. Zn-protein complexes); and/or non-ionic surfactants. The antibody can be formulated at a concentration of between 0.5-200 mg/ml, or between 10-50 mg/ml.

The compositions containing the EMP2 *Chlamydia* inhibitors of the invention (e.g., anti-EMP2 antibodies and EMP2 polypeptides) can be administered for therapeutic or prophylactic treatments. In therapeutic applications, compositions are administered to a patient having a *Chlamydia* infection in a "therapeutically effective dose." Single or multiple administrations of the compositions may be administered depending on the dosage and frequency as required and tolerated by the patient. A "patient" or "subject" for the purposes of the present invention includes both humans and other animals, particularly mammals. Thus the methods are applicable to both human therapy and veterinary applications. In the preferred embodiment the patient is a mammal, preferably a primate, and in the most preferred embodiment the patient is human.

The pharmaceutical compositions can comprise additional active agents, including any one or more of the following, analgesics, anti-inflammatories, antibiotics, antimicrobials, lubricants, contraceptives, spermicides, local anesthetics, and anti-puritics.

As used herein, the term "carrier" refers to a typically inert substance used as a diluent or vehicle for an active agent to be applied to a biological system in vivo or in vitro. (e.g., drug such as a therapeutic agent). The term also encompasses a typically inert substance that imparts cohesive qualities to the composition.

In some embodiments, the invention provides a composition comprising an EMP2 *Chiamydia* inhibitor and a physiologically acceptable carrier at the cellular or organismal level. Typically, a physiologically acceptable carrier is present in liquid, solid, or semi-solid form. Examples of liquid carriers include physiological saline, phosphate buffer, normal buffered saline (135-150 mM NaCl), water, buffered water, 0.4% saline, 0.3% glycine, glycoproteins to provide enhanced stability (e.g., albumin, lipoprotein, globulin, etc.), and the like. Examples of solid or semi-solid carriers include mannitol, sorbitol, xylitol, maltodextrin, lactose, dextrose, sucrose, glucose, inositol, powdered sugar, molasses, starch, cellulose, microcrystalline cellulose, polyvinylpyrrolidone, acacia gum, guar gum, tragacanth gum, alginate, extract of Irish moss, panwar gum, ghatti gum, mucilage of isapol husks, Veegum®, larch arabogalactan, gelatin, methylcellulose, ethylcellulose, carboxymethylcellulose, hydroxypropylmethylcellulose, polyacrylic acid (e.g., Carbopol), calcium silicate, calcium phosphate, dicalcium phosphate, calcium sulfate, kaolin, sodium chloride, polyethylene glycol, and combinations thereof. Since physiologically acceptable carriers are determined in part by the particular composition being administered as well as by the particular method used to administer the composition, there are a wide variety of suitable formulations of pharmaceutical compositions of the present invention (see, e.g., *Remington's Pharmaceutical Sciences,* $17^{th}$ ed., 1989). The carriers and compositions are preferably sterile.

The compositions of the present invention may be sterilized by conventional, well-known sterilization techniques or may be produced under sterile conditions. Aqueous solutions can be packaged for use or filtered under aseptic conditions and lyophilized, the lyophilized preparation being combined with a sterile aqueous solution prior to administration. The compositions can contain pharmaceutically or physiologically acceptable auxiliary substances as required to approximate physiological conditions, such as pH adjusting and buffering agents, tonicity adjusting agents, wetting agents, and the like, e.g., sodium acetate, sodium lactate, sodium chloride, potassium chloride, calcium chloride, sorbitan monolaurate, and triethanolamine oleate.

Formulations suitable for oral administration can comprise: (a) liquid solutions, such as an effective amount of a packaged platinum-based drug suspended in diluents, e.g., water, saline, or PEG 400; (b) capsules, sachets, or tablets, each containing a predetermined amount of a platinum-based drug, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise an EMP2 *Chlamydia* inhibitor in a flavor, e.g., sucrose, as well as pastilles comprising a polypeptide or peptide fragment in an inert base, such as gelatin and glycerin or sucrose and acacia emulsions, gels, and the like, containing, in addition to the inhibitor, carriers known in the art.

Topical Compositions

In preferred embodiments, the present invention provides topical pharmaceutical compositions comprising an EMP2 *Chlamydia* inhibitor according to the invention. More preferably, the inhibitor is a small organic compound, an EMP2 polypeptide, or anti-EMP2 antibody. The inhibitor may be in a unit dosage form comprising per unit dosage an amount of a EMP2 *Chlamydia* inhibitor as provided above which is effective for inhibiting infection by *Chlamydia*.

Also provided are methods of treating *Chlamydia* infections by topically administering an effective amount of such compositions (e.g., in unit dosage form) to, or proximal to, the affected area.

The EMP2 *Chlamydia* inhibitors may be formulated in combination with a pharmaceutically acceptable carrier. Dosage forms for the topical administration of the compounds of this invention include powders, sprays, foams, jellies, ointments, pastes, creams, lotions, gels, solutions, patches, suppositories and liposomal preparations. The dosage forms may be formulated with mucoadhesive polymers for sustained release of active ingredients at the urogenital area. The active compound may be mixed under sterile conditions with a pharmaceutically acceptable carrier, and with any preservatives, buffers, or propellants, which may be required. Topical preparations can be prepared by combining the inhibitor t with conventional pharmaceutical diluents and carriers commonly used in topical dry, liquid, cream and aerosol formulations. Ointment and creams may, for example, be formulated with an aqueous or oily base with the addition of suitable thickening and/or gelling agents. Such bases may include water and/or an oil such as liquid paraffin or a vegetable oil such as peanut oil or castor oil. Thickening agents which may be used according to the nature of the base include soft paraffin, aluminum stearate, cetostearyl alcohol, propylene glycol, polyethylene glycols, woolfat, hydrogenated lanolin, beeswax, and the like. Lotions may be formulated with an aqueous or oily base and, in general, also include one or more of the following: stabilizing agents, emulsifying agents, dispersing agents, suspending agents, thickening agents, coloring agents, perfumes, and the like. Powders may be formed with the aid of any suitable powder base, e.g., talc, lactose, starch, and the like. Drops may be formulated with an aqueous base or nonaqueous base also comprising one or more dispersing agents, suspending agents, solubilizing agents, and the like.

The ointments, pastes, creams and gels also may contain excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays also can contain excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

In some embodiments, the EMP2 *Chlamydia* inhibitor is formulated with a pharmaceutically acceptable carrier and at least one of the following second pharmacologic agents: a local anesthetic (e.g., lidocaine, prilocaine, etc.), local anti-inflammatory agent (e.g., naproxen, pramoxicam, etc.), corticosteroid (e.g., cortisone, hydrocortisone, etc.), anti-itch agent (e.g., loperamide, diphylenoxalate, etc.), an agent that interferes with the activation of peripheral sensory neurons, including divalent and trivalent metal ions (e.g., manganese, calcium, strontium, nickel, lanthanum, cerium, zinc, etc.), analgesic agents, a lubricant, yeast-based product (e.g., lyophilized yeast, yeast extract, etc.), a spermicide, growth-promoting and/or wound healing-promoting agent known to promote re-epithelialization (e.g., platelet-derived growth factor (PDGF), interleukin-11 (IL-11), etc.), anti-microbial agent (e.g., Neosporin, polymyxin B sulfate, bacitracin zinc, etc.), mucoadhesive agent (e.g., cellulose derivatives, etc.), cytoprotectant agent (e.g., colloidal bismuth, misoprostol, sucralfate, etc.) as defined in Goodman and Gilman, *The Pharmacological Basis of Therapeutics*, or menthol.

The EMP2 *Chlamydia* inhibitor may be present in the composition in unit dosage form effective for the treatment of the *Chlamydia* infection. The at least one second pharmacological compound is typically present in the composition in unit dosage effective for the treatment of a a condition(s), symptom(s) or effect(s) associated with or resulting from the *Chlamydia* infection or activity related to its transmission. The topical pharmaceutical compositions also can contain other active ingredients such as antimicrobial agents, particularly antibiotics, anesthetics, analgesics, contraceptive agents, lubricants, spermicides, and antipruritic agents. The topical pharmaceutical compositions can also include one or more preservatives or bacteriostatic agents, e.g., methyl hydroxybenzoate, propyl hydroxybenzoate, chlorocresol, benzalkonium chlorides, and the like. The topical composition may be applied with an applicator, may be coated on either or both surfaces of a condom or diaphragm or other contraceptive device. Particularly preferred antibiotics are those conventionally used to treat a *Chlamydia* infection.

The dosage of a EMP2 *Chlamydia* inhibitor depends upon many factors that are well known to those skilled in the art, for example, the particular compound; the condition being treated; the age, weight, and clinical condition of the recipient patient; and the experience and judgment of the clinician or practitioner administering the therapy. An effective amount of the compound is that which provides either subjective relief of symptoms or an objectively identifiable improvement as noted by the clinician or other qualified observer. The dosing range varies with the compound used, the route of administration and the potency of the particular compound.

In yet other embodiments, the invention provides topical sustained and prolonged release pharmaceutical compositions comprising one or more pharmacological compounds described supra, and a pharmaceutically acceptable carrier, to treat a *Chlamydia* infection. Preferably, the compositions are administered in unit dosage form to a subject in need of such treatment. Topical sustained and prolonged release compositions are typically variants which include 1) an absorbent in a hydrophilic base; 2) an absorbent in a hydrophobic base; and 3) coated beads containing an absorbent matrix dispersed in a suitable vehicle.

Such hydrophilic compositions and preparations of the invention comprise a compound of the invention and a polymer, such as cellulose (methyl cellulose, ethyl cellulose, hydroxy propyl cellulose, etc.), higher molecular weight polyethylene glycol, methacrylic-acrylic acid emulsion, hydrogel, carbopol, ethyl vinyl acetate copolymer, or polyester, etc., to bind the compound of interest to the polymer. The compound-polymer matrix is then dispersed in a hydrophilic vehicle to form a semi-solid. After administration of such hydrophilic composition into the appropriate urogenital area, such as, e.g., the vagina or urethral tract, the water in the semi-solid preparation is adsorbed and the polymer matrix with the active ingredient (i.e., the pharmaceutical compound) remains as a coating in the area to which it has been applied. The pharmaceutical compound is then slowly released from this coating.

Hydrophobic compositions and preparations of the invention employ similar polymers as used in the hydrophilic preparations, but the polymer/compound matrix is dispersed into a vehicle, such a plastibase, in the hydrophobic compositions and preparations. Plastibase is a mineral oil base that only partially dissolves the pharmaceutical compound. The semi-solid composition forms a thin coating on the urogenital region to which the composition has been applied (such as, e.g., the vagina or urethral tract) and slowly releases the active compound. The prolonged action is controlled principally by the solubility of the active ingredient in the vehicle.

The present invention also provides coated beads which are produced by first absorbing a compound of the present invention, or a combination of compounds, on a cellulosic material blended with polyethylene glycol, filler, binder and other excipients. The resulting matrix is then extruded and spheronized (e.g., the process of making into spheres) to create small beads. The beads are then coated to an appropriate thickness with one or more of a suitable material, such as a methacrylic-acrylic polymer, polyurethane, ethyl vinyl acetate copolymer, polyester, silastic, etc. The coating on the beads acts as a rate controlling membrane that regulates the release of the compound from the core beads.

Methods of Treatment

The terms "treating" or "treatment" of *Chlamydia* includes:

(1) preventing the disease, i.e., causing the clinical symptoms of the disease not to develop in a mammal that may be exposed to the organism but does not yet experience or display symptoms of the disease, (2) inhibiting the disease, i.e., arresting or reducing the development of the disease or its clinical symptoms, or eliminating the infection or reducing the numbers of *Chlamydia* in the subject or infected tissue.

(3) relieving the disease, i.e., causing regression of the disease or its clinical symptoms.

The EMP2 *Chlamydia* inhibitors and pharmaceutical compositions according to the invention may be administered by any route of administration (e.g., intravenous, topical, intraperitoneal, parenteral, oral, intravaginal, rectal, occularly) to treat a subject for *Chlamydia*. They may be administered as a bolus or by continuous infusion over a period of time, by intramuscular, intraperitoneal, intracerobrospinal, subcutaneous, intra-articular, intrasynovial, intrathecal, oral, topical, or inhalation routes. Intravenous or subcutaneous administration of the antibody is preferred. The administration may be local or systemic. They may be administered to a subject who has been diagnosed with a *Chlamydia* infection, a history of infection, or engages in activities wherein exposure to *Chlamydia* may occur. They may be administered to a subject whose infection has been difficult to control or recurs after convention antibiotic therapy. They may be administered in conjuction with conventional antibiotic therapy for *Chlamydia* or with contraceptive agents. In some embodiments, the methods include the step of first diagnosing the subject as having a *Chlamydia* infection and then administering the EMP2 *Chlamydia* inhibitor according to the invention. In some further embodiments, the diagnosis is achieved as described below.

In some embodiments, the EMP2 *Chlamydia* inhibitors are used to treat chronic pelvic pain syndromes in a subject with *Chlamydia* infection. The inhibitors in some other embodiments are used to treat ocular infections with *Chlamydia* or trachoma, the primary cause of infectious blindness worldwide. In yet other embodiments, the inhibitors are used to treat inflammatory diseases (e.g., arthritis, arteriosclerosis) in a subject having a *Chlamydia* infection.

The siRNA and ribozyme EMP2 *Chlamydia* inhibitor formulations of the invention may be administered to a cell. The cell can be provided as part of a tissue, such as an epithelial membrane, or as an isolated cell, such as in tissue culture. The cell can be provided in vivo, ex vivo, or in vitro. The formulations can be introduced into the tissue of interest in vivo or ex vivo by a variety of methods. In some embodiments of the invention, the nucleic acids of the invention are introduced into cells by such methods as microinjection, calcium phosphate precipitation, liposome fusion, or biolistics. In further embodiments, the nucleic acids are taken up directly by the tissue of interest.

Diagnosis of *Chlamydia* Infection

Diagnosis is based upon symptoms and detection of the bacteria in body fluids or samples as is known to one of ordinary skill in the art. The traditional method of diagnosis is inoculation of monolayer cell culture with clinical specimens, followed by staining and visual examination after 2-3 days. Another more routine method requires the measurement of antichlamydial antibody titer changes in the paired sera (four fold greater rise in titer) and has a low predictive value for ongoing infection. Direct tests such as ELISA and IF (immunofluorescence) are easier to perform and require less time and labor than culturing of the organism. These methods directly measure *Chlamydia* antigens. The antigens used for the serological identification and differentiation of *Chlamydiae* are cell envelope antigens which are species specific. This antigens can distinguish *C. trachomatis*, *C. psittaci* and *C. pneumoniae* and among the 15 serovars of *C. trachomatis* (serovar specific antigens). (see, for instance, Black, C. M., *Clin Microbiol Rev* 10: 160-184 (1997)). In addition, DNA amplification methods are commercially available for the detection of *Chlamydia* specific RNA and DNA in body fluids.

EXAMPLES

The following examples are offered to illustrate, but not to limit the claimed invention.

Example 1

Methods for Studying Chlamydial Infectivity and EMP2 Chlamydial Inhibitors

A. Endometrial Cell Lines and *Chlamydia* Strains.

The human endometrial adenocarcinoma cell line HEC1A (HTB112, ATCC, Manassas, Va.) was cultured in McCoy 5a media (Invitrogen, Carlsbad, Calif.) supplemented with 10% fetal calf serum (Hyclone, Logan, Utah) at 37° C. in a humidified 5% $CO_2$ and passaged every 7 days. EMP2-modulated HEC1A sublines were stable transfectants with expression plasmids for GFP, a human EMP2-GFP fusion protein, or a human EMP2-specific ribozyme (HEC1A-GFP, HEC1A-hEMP2, and HEC1A-hRV2). EMP2 protein expression levels relative to HEC1A-GFP were 1.0, 8.7, and 0.2, respectively.

An 8-strain mix of human *C. trachomatis* (serovars D, E, F, and K) and *C. muridarum* were purified, aliquoted, and stored at −80° C. until ready for use (see, Caldwell, H. D., et al., Infect Immun 31, 1161-76 (1981). All *Chlamydia* samples were made in Eagle MEM (Invitrogen) with 10% fetal calf serum (Atlanta Biologicals, GA), 3 mg/ml glucose (Fisher Scientific, PA), 1.25 µg/ml Fungizone (Invitrogen), 100 µg/ml Vancomycin (Invitrogen), 100 µg/ml gentamicin (Invitrogen), and 0.5 µg/ml cycloheximide (Sigma, St. Louis, Mo.) and kept on ice until use.

B. Antibodies and Peptides.

Antibodies to human EMP2 were produced by immunization of rabbits with EDIHDKNAKFYPVTREGSYG (SEQ ID NO:2), a peptide in the second extracellular loop of human EMP2 (see, Wang, C. X., et al., Blood 97, 3890-5 (2001)). In peptide blocking experiments, this peptide was used to assure specificity of binding whereas a control 20mer peptide from the first extracellular loop of human EMP2 was used as a negative control. Antibody from the pre-immune rabbits was used as a negative control. For immunohistochemical detection of *Chlamydia* EBs or inclusions, an anti-*Chlamydia* LPS mouse antibody (clone EV1-H1) was used as kindly provided by Dr. Harlan Caldwall (Laboratory of Intracellular Parasites, National Institutes of Health, Hamilton, Mont.). FITC- and Texas Red-conjugated goat anti-rabbit IgG was from Jackson Immunotech (West Grove, Pa.); FITC anti-mouse IgG, and horseradish peroxidase-conjugated anti-rabbit or anti-mouse IgG antibody were from Southern Biotechnology Associates, Birmingham, Ala.). Rabbit anti-human β-actin was from Sigma.

C. *Chlamydia* Infection.

HEC1A cells were plated at a concentration of $2.5 \times 10^5$ cells/ml and incubated overnight to establish mono-layers. Infection with *C. trachomatis* or *C. muridarum* at multiplicity of infection (MOI) of 0.5-3.0 was performed in media containing cycloheximide at 35° C. with 5% $CO_2$ for 24 hours. Cells were fixed in methanol and inclusion bodies were identified immunohistochemically using mouse anti-Chlamydia LPS and FITC anti-mouse IgG secondary antibody. Cells were counter stained with Evans Blue, mounted in glycerol, and scored using fluorescence microscopy. For the antibody study, cells were incubated with antibody for 1 hour at 37° C. before the infection step. For peptide blocking, antibody was mixed with peptide at indicated concentrations for 1 hour at room temperature prior to addition to cell cultures.

D. *Chlamydia* Attachment.

HEC1A cells were plated at $1 \times 10^4$ cells/ml and incubated overnight. Cells were infected with *C. trachomatis* at MOI of 50. Cells were then incubated for 1.5 hrs at 4° C. Attached *Chlamydia* elementary bodies were identified using immunohistochemistry as described above, and counted with fluorescent microscopy (magnification, 1000×). For the antibody studies, cells were treated as described above.

E. Fluorescence Microscopy.

*Chlamydia* inclusions and elementary bodies were identified with an epiillumination fluorescent microscope (Olympus, Melville, N.Y.) using FITC and Texas Red filters. *Chlamydia* inclusions were defined by round, regular shape, with a diameter of approximately ⅓ of cell size. In order to prevent biased counting, the plates were scored in a masked fashion by at least two independent observers. 5-10 random fields were selected from each well and the total number of cells with inclusions (C1) and without inclusions (C0) were counted. The rate of infection was calculated (C1/(C1+C0)×100) from these numbers. For the attachment study, the number of elementary bodies on the cell membrane of 100 cells/slide was counted in a masked fashion. Areas with clustered cells or indistinguishable inclusions were not counted. Experiments were performed with 2-3 replicate samples, and repeated at least three times.

F. Western Immunoblots.

Cellular lysates in Laemmli buffer were treated with peptide-N-glycosidase F (PNGase; New England Biolabs, Beverly, Mass.) to remove N-linked glycans to convert the heterogeneously glycosylated protein into a single ~20 kDa species. Proteins were separated by SDS-PAGE as previously described (see, Wadehra, M., et al., Mol Biol Cell 15: 2073-2083 (2004), and Wang, C. X., et al., Blood 97: 3890-5 (2001)). Blots were probed with anti-EMP2 or anti-β-actin followed by incubation with a horseradish peroxidase-conjugated anti-rabbit or anti-mouse IgG antibody. Proteins were visualized by chemiluminescence (ECL; Amersham Biosciences, Piscataway, N.J.). Negative controls (secondary antibodies alone) produced no signal. Experiments were repeated at least three times.

G. Lipid Raft Fractionation.

$5 \times 10^7$ cells were harvested, washed in PBS, and then resuspended in Tris-buffered saline (50 mM Tris, pH 7.5, 20 mM EDTA, 10/1 g/ml aprotinin, 10 µg/ml leupeptin, 1 mM phenylmethylsuflonyl fluoride, and 1 mM $Na_2VO_3$. Cells were lysed by sonication (see, Wadehra, M., et al., Mol Biol Cell 15: 2073-2083 (2004) and Moran, M. et al., Immunity 9: 787-96 (1988)) and then dissolved in 1% Triton X-100 or 1% Brij 58 on ice for 60 min. The sample was mixed 1:1 with 80% sucrose (40% final), followed by step overlays with 35 and 5% sucrose. The gradient was centrifuged at 46,000 rpm for 18 h with a Sorvall SW55 rotor, and fractions (400 µl) were collected from the top of the gradient. Samples were then solubilized in Laemmli buffer, treated with PNGase to remove N-glycans, and analyzed by SDS-PAGE. Cholesterol depletion was performed as described previously (see, Claas, C., et al., J Biol Chem 276: 7974-84 (2001)). Briefly, cells were washed in PBS to remove serum and then incubated in DMEM containing 20 mM methyl-β-cyclodextrin (Sigma) for 60 min at 37° C. In order to insure a lack of toxicity, cells were analyzed by trypan blue exclusion prior to harvesting. Samples were then treated as described above.

H. Statistical Analysis.

For the anti-EMP2 antibody and EMP2 peptide studies, groups were analyzed by two-tailed Student's paired t test, with a significance level of $p \leq 0.05$. The statistical significance of infection and attachment rate on stably transfected cells was tested using two-tailed two-sample equal variance t-test with a confidence level of $p \leq 0.05$.

Example 2

Localization of EMP2 to Lipid Rafts

To assess whether EMP2 is localized to lipid raft domains in endometrial cells (a Chlamydial host target), EMP2 was evaluated in the HEC1A human endometrial cancer cell line by lipid raft fractionation with Brij 58 and Triton X-100. In HEC1A cells, EMP2 localized to the light, detergent-resistant gradient fractions coinciding with GM1 ganglioside, a lipid raft component (FIG. 1a,b). To confirm the localization of EMP2 to lipid rafts, lysates were prepared in 1% Triton X-100 in the presence or absence of methyl-β-cyclodextrins (MβCD) that selectively deplete cholesterol from cellular membranes and causes loss of protein localization into lipid rafts. In 1% Triton X-100, EMP2 localized to both light, detergent-resistant fractions 3-4 as well as dense fractions 6-7 (FIG. 1c). When cells were incubated for 60 minutes with MβCD in serum free conditions, EMP2 expression completely shifted to soluble, dense fractions in the presence of 1% Triton X-100 (fractions 7-10). Repletion of cholesterol in MβCD-treated cells partially restored EMP2 to the lipid raft fractions. These data indicate that, in HEC1A cells, EMP2 mainly resides within lipid raft microdomains, which are thought to be the microanatomic target for *Chlamydia*-host cell interaction.

Example 3

Effect of Anti-EMP2 Antibody on *Chlamydia* Infectivity

Figure 2:
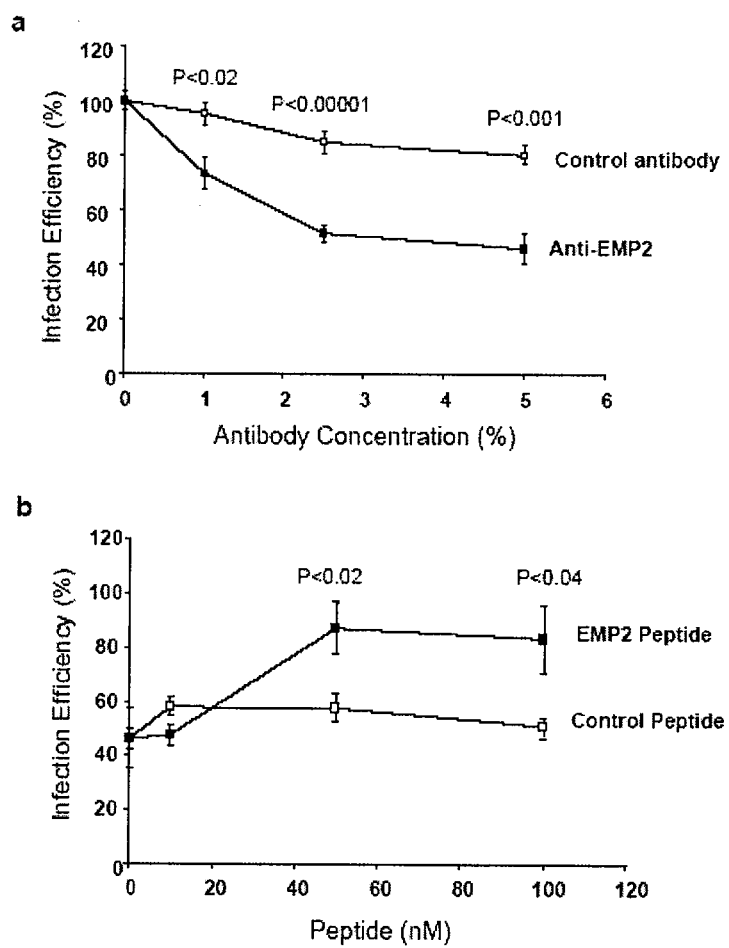
FIG. 2. illustrates anti-EMP2 antibody inhibition of Chlamydial infection. (a) Effect of anti-EMP2 antibody. HEC1A were infected with *C. trachomatis* (an 8-strain mix of human serovars D-K) in the presence of indicated concentrations of anti-EMP2 or control pre-immune antibody. Chlamydial infection efficiency (% *Chlamydia* inclusions compared to untreated cells) was determined by immunostaining (mean±SEM), and compared at each antibody concentration by student's t test. (b) Effect of EMP2 peptide on anti-EMP2 inhibition. Anti-EMP2 (5%) was pretreated with indicated concentrations of specific EMP2 (second extracellular loop) peptide or control peptide, and then coincubated with cells during *Chlamydia* infection. Infection efficiency was normalized to *Chlamydia* inclusions in cells without peptide treatment, and compared at each concentration of EMP2 or control peptide. Results are representative of 2 or more independent experiments.

The lipid raft localization of EMP2 in endometrial cells and its control of lipid raft trafficking by integrins, caveolins, and glycosylphosphatidyl inositol-linked proteins (18, 20, 21), raised the possibility that EMP2 might directly or indirectly affect Chlamydial infectivity. To begin testing this hypothesis, anti-EMP2 antibody (specific for the 2nd extracellular loop of EMP2) was added to HEC1A cell cultures, then incubated with *C. trachomatis*, and infection was measured (Chlamydial inclusions, expressed as "infection efficiency", % inclusions relative to HEC1A cells without antibody treatment) (FIG. 2a). Anti-EMP2 antibody produced a dose-dependent inhibition of infection efficiency (reaching less than 50% of HEC1A cells without antibody), at levels that were highly significant compared to control antibody. To determine if the observed inhibition was due to EMP2 specificity, anti-EMP2 was pre-incubated with the relevant second extracellular loop EMP2 peptide, or a control peptide (first extracellular loop) (FIG. 2b). Pre-incubation of anti-EMP2 antibody with the specific EMP2 peptide neutralized the blocking effect of anti-EMP2 antibody, significantly increasing *Chlamydia* infection efficiency. In contrast, the control peptide at the same concentrations did not significantly increase *Chlamydia* infection in the presence of anti-EMP2. Thus, the anti-EMP2 effect on *Chlamydia* infection reflected its specificity for the second extracellular loop of EMP2.

Example 4

Efficiency of *Chlamydia* Infection with EMP2 Expression

Figure 3:
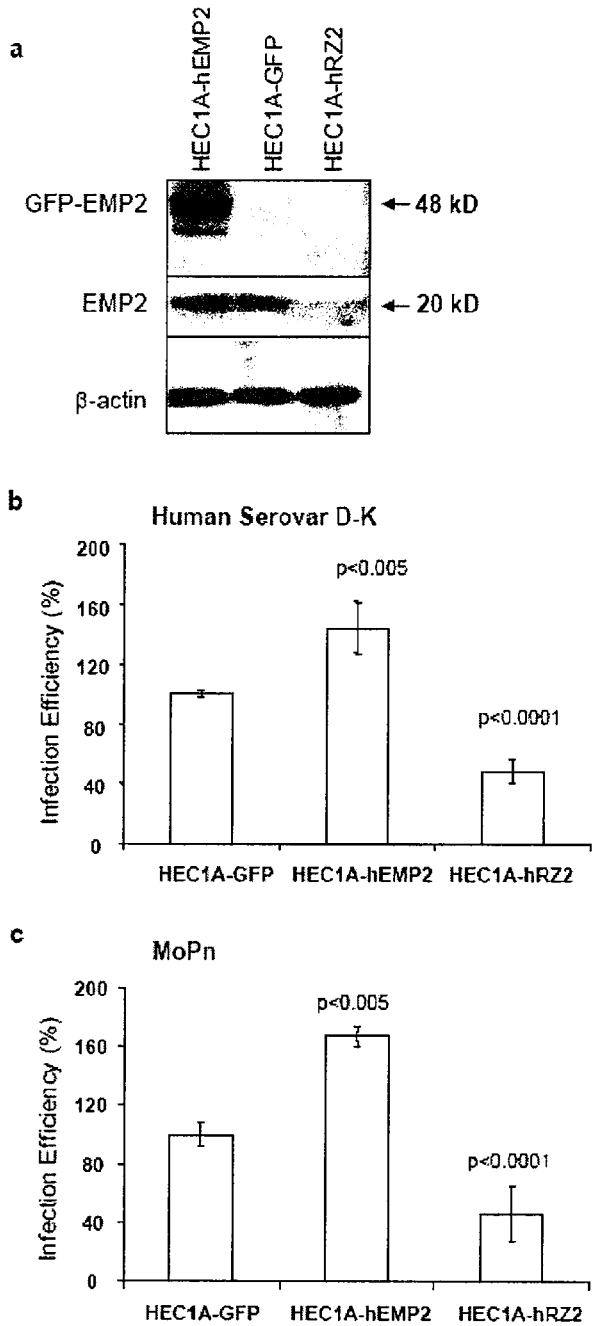
FIG. 3 illustrates EMP2 expression levels positively correlate with Chlamydial infection efficiency. (a) EMP2 levels were compared by anti-EMP2 western immunoblot in HEC1A cells stably transfected with plasmids for expression of a human EMP2-GFP fusion protein (HEC1A-hEMP2), GFP (HEC1A-GFP), or a EMP2-specific ribozyme (HEC1A-hRZ2). Shorter and longer exposures are shown for the hEMP2-GFP fusion protein (48 kDa) and native EMP2 (20 kDa), respectively. Western immunoblot for β-actin is shown as a loading control. (b, c) Cells were infected with (b) *C. trachomatis* (a mixture of 8 strains comprising serovars D-K) or (c) *C. muridarum* (MoPn), and *Chlamydia* inclusions (% HEC1A-GFP control cells) were scored (mean±SEM) and compared by student's t test to HEC1A-GFP. Data in (b) and (c) are compiled from 5 independent experiments, and each experiment had at least three replicate groups.

As another experimental test, the efficiency of *Chlamydia* infection in endometrial cells was examined to see if it varied with EMP2 expression. HEC1A cell lines were stably transfected with expression plasmids to overexpress an EMP2 fusion protein (HEC1A-hEMP2), suppress expression of native EMP2 via an EMP2-specific ribozyme (HEC1A-hRZ2), or a control GFP transfectant (HEC1A-GFP) (FIG. 3a). A recent quantitative study showed that EMP2 levels in these overexpressing and ribozyme HEC1A sublines were respectively 8.7-fold and 0.2-fold compared to GFP control cells (data not shown). The three HEC1A sublines were infected with *C. trachomatis* (FIG. 3b), and Chlamydial infection was quantitated. Compared to control HEC1A-GFP cells, EMP2-overexpressing HEC1A-hEMP2 cells had increased infection efficiency (145%, p<0.005). Reciprocally, EMP2-underexpressing HEC1A-hRV2 cells were impaired for infection efficiency (49%, p<0.0001). Similar results were obtained using a distinct *Chlamydia* species, *C. muridarum* (MoPn) (FIG. 3c). Compared to HEC1A-GFP, infection in HEC1A-hEMP2 cells was increased (167%, p<0.005), and in HEC1A-hRV2 was decreased (46%, p<0.0001).

Example 5

EMP2 Directly Mediates *Chlamydia* Attachment

Figure 4:
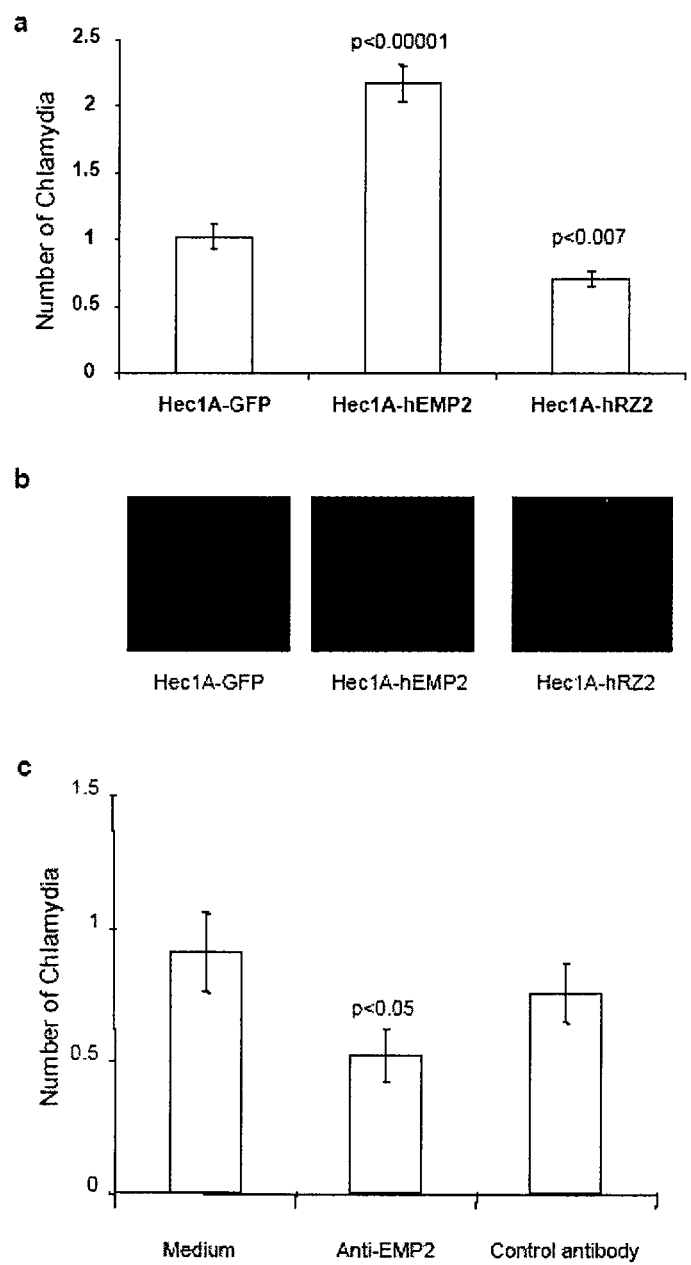
FIG. 4 illustrates EMP2 affects Chlamydia EB attachment. (a) HEC1A-GFP, HEC1A-hEMP2, and HEC1A-hRZ2 were incubated with *C. trachomatis* EBs for 1.5 hrs at 4° C., and the number of attached EB per cell was scored by immunofluorescence with anti-Chlamydial LPS. Values are mean±SEM. More than 800 cells scored per experimental group, and 4 independent experiments were performed. Groups were compared to HEC1A-GFP by equal variance t-test. (b) Representative immunofluorescence microscopy (magnification, 1000×) of HEC1A sublines after EB attachment, stained for EB (anti-Chlamydial LPS; Texas Red), F-actin (FITC-phalloidin), and nuclei (DAPI, blue). (c) HEC1A cells were incubated with *Chlamydia* EB alone (medium), or in the presence of anti-EMP2 or control antibody (2.5%). EB attachment was analyzed as in FIG. 4a; anti-EMP2 and control antibody groups were statistically compared to the medium alone group.

The above findings indicated that *Chlamydia* infection efficiency was dependent on the level of EMP2 expression, in a manner that could be blocked by anti-EMP2 antibody. While EMP2 might affect various stages of the infection process, one possible mechanism is that EMP2 acts at the initial attachment step. To test this prediction, EMP2-divergent Hec1A sublines were incubated with *Chlamydia* EBs in the cold, and the number of surface-attached EBs were quantitated. Compared to HEC1A-GFP, EB attachment in HEC1A-hEMP2 cells was increased (230%, p<0.0001). Reciprocally, attachment in HEC1A-hRV2 cells was decreased (70%, p<0.05). Representative images of EB attachment to these cell lines are shown in FIG. 4b. EB attachment was also inhibited by anti-EMP2 antibody. Compared to medium only, anti-EMP2 reduced EB attachment (50%, p<0.05); control antibody had no effect (FIG. 4c). These finding indicate that EMP2 directly affects EB attachment.

Example 6

Use of Phage Display Methodology to Obtain Antibodies

Phage display, first established by Smith et al in 1985, can provide an in vitro immune system useful in creating high affinity antibodies to virtually any antigens with a bare minimal recognition region. Selection of antibody using phage antibody libraries with filamentous phase and phagemids mimics humoral immune system that lack cell-mediated responses. Thus, generation of purified antibodies with affinities comparable to ones made by conventional hybridoma technology can be achieved without complications such as self-tolerance, T cell help and antigen presentation (see, Bradbury, A. R. et al., *J Immunol Methods* 290: 29-49 (2004); Marks, J. D. et al., *Methods Mol Biol* 248: 161-76 (2004); Pavlik, P. et al., *Hum Antibodies* 12: 99-112 (2003); Persic, L. et al., *FEBS Lett* 443, 112-6 (1999); and 5. Smith, G. P., *Science* 228, 1315-7 (1985)).

For the selection of antibodies against mouse and human epithelial membrane protein-2 (mEMP2 and hEMP2 respectively), a purified phage antibody library expressing a single chain Fv (scFv) with the two V regions linked with a flexible linker is used. V genes may be derived from naturally rearranged V regions found in B-cells and scFv is expressed on pIII, a bacteriophage coat protein.

20 amino acid sequences from the extracellular loop of mEMP2 and hEMP2 such as previously used for polyclonal antibody production are chosen for antigen targets for the phage display. Successful scFv isolation against 20-mer peptide has been previously reported. In order to maintain natural conformation, these peptides are biotinylated at C- and N-termini with 4 amino acid long linkers (GSGS; SEQ ID NO:8). 3 rounds of selection using streptavidin and avidin-coated beads are carried out for each sample to isolate high affinity antibodies as previously described. Input and output concentrations of phage antibody libraries and values for recovery and enrichment for each round are calculated.

The specificity of selected antibodies is tested by ELISA, in which 95 colonies picked from the isolated phage populations are incubated with bound mEMP2/hEMP2 peptides on streptavidin coated plates. Most of colonies may show a 4-5 fold increase in reactivity compared to control, indicating their high specificity against antigens. C-mEMP2 samples are used for further identification of anti-mEMP2 antibodies.

Figure 5:
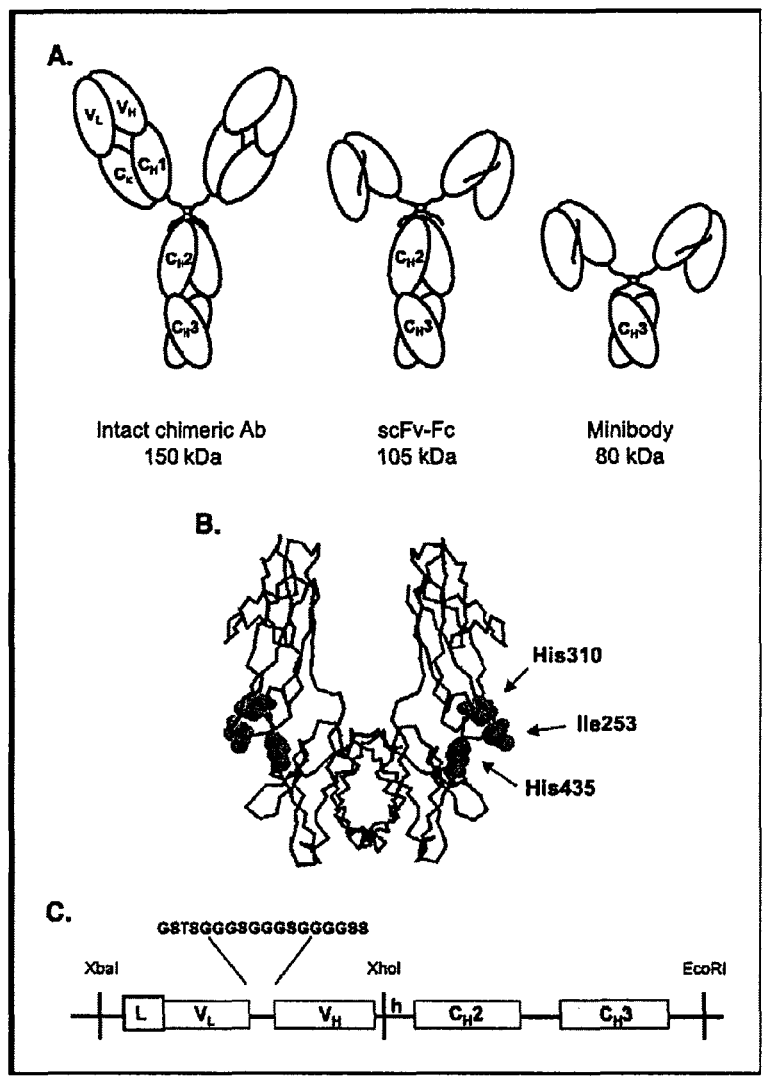
FIG. 5 depicts a chimeric antibody for use according to the invention as may be made by use of phage display methodology. GSTSGGGSGGGSGGGSS=SEQ ID NO:4.

Of the highly reactive colonies, 14 colonies/sample are chosen for DNA fingerprinting and subsequent DNA sequence analysis. Protein expression and purification systems are developed for each antibody using H is containing expression vectors, and testing the specificity and affinity of these antibodies is tested via Flow cytometry and Western Blot. Once validity of these antibodies is confirmed, these scFvs are fused to intact Fc region containing $C_H1$, $C_H2$ and/or $C_H3$ domains to produce intact chimeric antibody (see FIG. 5). Useful laboratory methods for performing the above are further disclosed in Bird, R. et al., *Trends Biotechnol* 9: 132-7 (1991); Huston, J. S. et al., *Proc Natl Acad Sci USA* 85: 5879-83 (1988); Wang, C. X., et al., *Blood* 97: 3890-5 (2001); Griffiths, A. D. et al., *Embo J* 12: 725-34 (1993); Kenanova, V. et al., *Cancer Res* 65: 622-31 (2005); Slavin-Chiorini, D. C. et al., Cancer Res 55: 5957s-5967s (1995); and Xu, X. et al., *Cancer Res* 60, 4475-84 (2000).

The Fc-fused antibodies stabilize the antibodies, almost to a degree to natural antibodies but also allow one to detect the antibodies with anti-Fc secondary antibodies conjugated with detectable markers. Thus, the development of these antibodies will provide strong biochemical and therapeutic tools by producing highly purified stable anti-EMP2 antibodies with increased specificity (see, Slavin-Chiorini, D. C. et al., Cancer Res 55: 5957s-5967s (1995); and Xu, X. et al., *Cancer Res* 60: 4475-84 (2000)).

Example 7

Use of an Anti-EMP2 Diabody to Prevent, Reduce or Treat *Chlamydia* Infections in the Female Genital Tract (FGT)

Figure 6:
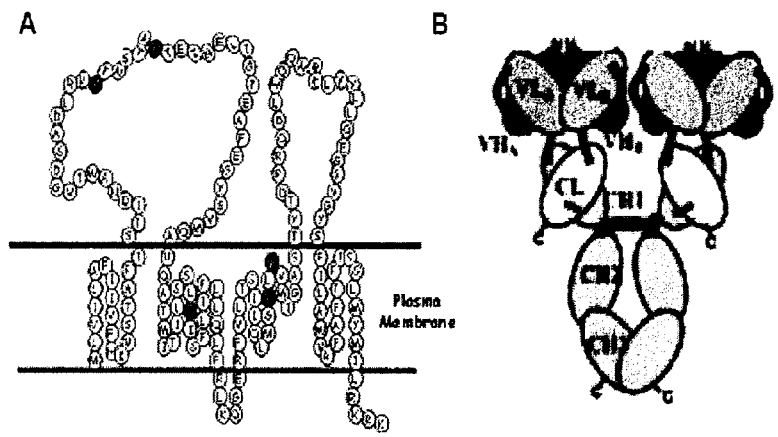
FIG. 6: (A) Sequence (SEQ ID NO:5) and structure of EMP2 molecule. A 24 amino acid peptide from the small extracellular loop was used to generate the anti-EMP2 recombinant Abs. (B) Example of a single chain diabody with two V regions (40)(4).

EMP2 is a transmembrane protein in the GAS-PMP22 family with 4 transmembrane domains and two extracellular loops (FIG. 6A). EMP2 is expressed in murine and human epithelial cell lines. EMP2 is expressed within the murine reproductive tract and ovaries and mediates blastocyst implantation via αVβ3 integrin. In order to extend our in vitro studies to an in vivo model of *Chlamydia* genital infection, an anti-EMP2 antibody was generated that could be purified to homogeneity. Recombinant monoclonal antibodies against EMP2 were created using a 24 amino acid sequence from the small extracellular loop of murine EMP2 (FIG. 1A), the area previously used to create the polyclonal antibody used in our report (Shimazaki et al., *Microbes Infect* 9:1003-10 (2007)). Recombinant monoclonal antibodies have been shown to have peptide affinities comparable to ones made by conventional hybridoma technology, but can be achieved without complications such as self-tolerance, T cell help and antigen presentation (Bradbury & Marks, *J Immunol Methods* 290: 29-49 (2004)).

In order to select for antibodies against mouse EMP2, a purified phage antibody library expressing a single chain Fv(scFv) with the two V regions linked with a flexible linker was used (gift from Dr. James D. Marks) (Bradbury & Marks, *J Immunol Methods* 290:29-49 (2004)). This resulted in a diabody molecule directed against mouse EMP2 (EMP2 diabody) as shown in FIG. 6B.

Figure 7:
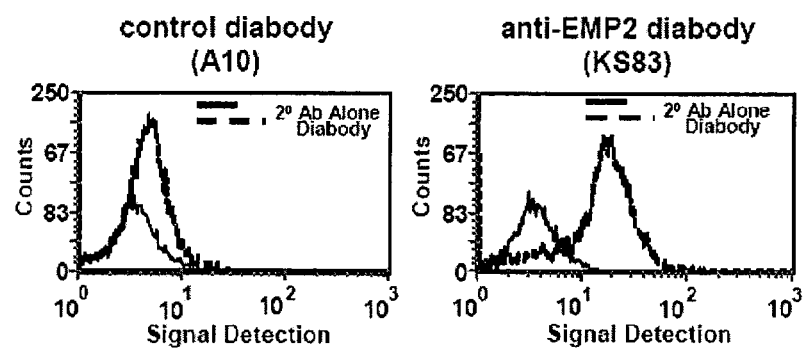
FIG. 7: Flow cytometry showing reactivity against the EMP2 expressing cells with the anti-EMP2 diabody (clone KS83) and no reactivity with a control diabody (clone A10).

Several molecularly-independent clones were observed to have high affinity for mouse EMP2 by ELISA (>5 fold) and five independent diabodies or recombinantly engineered divalent antibody fragments, were created, four with specificity against EMP2 (KS41, KS49, KS83, KS89), and a control diabody that does not recognize EMP2 (A10). The specificity of these diabodies, both reactivity against EMP2 for the KS series and no reactivity against EMP2 for the control A10 were verified by ELISA against the specific peptide used to select the antibody and by flow cytometry using cells that are known to either express EMP2 or lack EMP2 expression. FIG. 7 shows a representative flow cytometry confirmation of reactivity.

Figure 8:
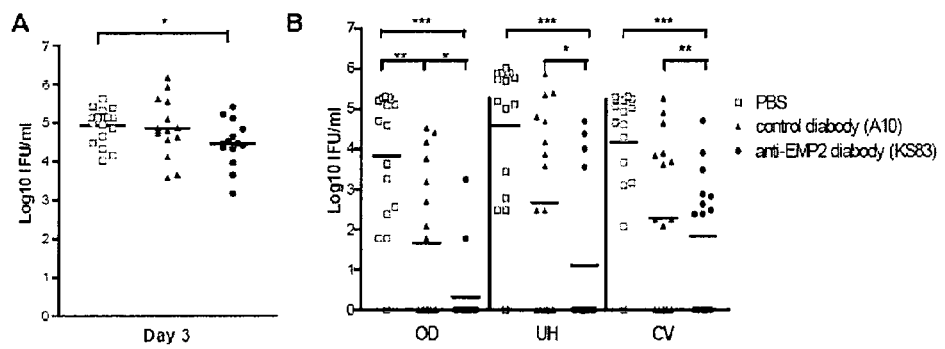
FIG. 8: Mice were hormonally synchronized and vaginally pretreated with PBS, 10 μg/mouse of control or anti-EMP2 diabody (clone KS83) and mice were infected (day 0) with MoPn as described in the text. A) Swabs were collected 3 days after infection and B) regions of the FGT: OD, oviducts; UH, uterine horn and CV, cervical-vaginal, were collected the following day, homogenized, and IFUs determined. Brackets indicate statistical comparisons, *p<0.05, p<0.005, *p<0.0001 by two-tailed Student's t test, n=16/grp. Data are compiled from 2 experiments.

Masking EMP2 Reduces the Local Bacterial Load of *Chlamydia muridarum* (MoPn) In Vivo We have recently reported that preventing the ligation of EMP2 or an associated complex on a variety of host cells in vitro with MoPn significantly blocked the organism's ability to infect various cell lines (Shimazaki et al., *Microbes Infect* 9:1003-10 (2007)). Whether blocking EMP2 on epithelial cells in the murine FGT could affect subsequent bacterial burden in vivo was next investigated. Mice were synchronized by administering progesterone by subcutaneous injection of 2.5 mg/mouse Depo-Provera 7 days prior to infection. This treatment is necessary in mice to avoid keratinizing epithelial cells and facilitate MoPn infectivity. Groups of mice were either vaginally pretreated with an anti-EMP2 diabody, a control diabody or the vehicle alone, PBS, for 20 minutes and then infected by vaginal deposition of $1.5 \times 10^5$ infectious forming units (IFU) *C. muridarum* (MoPn). As can be appreciated in FIG. 8A, a single pretreatment with a small amount of anti-EMP2 diabody significantly reduced initial infection levels in the FGT as determined from vaginal swabs taken every 3rd day. Tissue was collected from 3 regions of the FGT; oviducts (OD), uterine horns (UH) and cervical-vaginal (CV) region which includes the endocervix as previously described. Examination of bacterial burden in FGT regions revealed a significant decrease in MoPn levels compared to mice pretreated with control diabody. Further, pretreatment with anti-EMP2 diabody reduced ascending infection since the majority of anti-EMP2 diabody treated mice were negative for MoPn (FIG. 8B).

Figure 9:
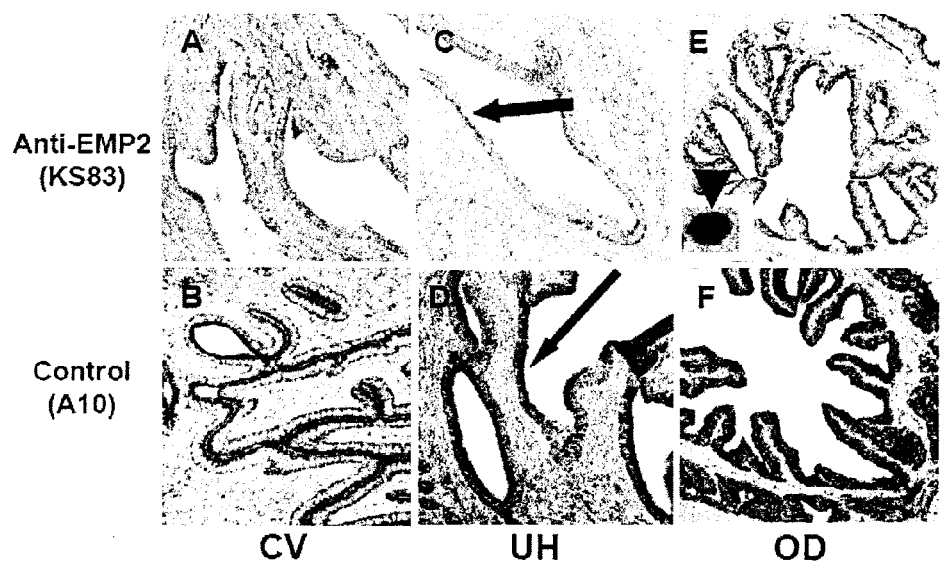
FIG. 9: The GT regions from mice pretreated as above with anti-EMP2 diabody KS83 (A, C & E) or control A10 (B, D & F) were harvested after 24 hours and IHC staining was performed on formalin-fixed, paraffin-embedded sections with a 1:500 dilution of anti-EMP2 immune sera. Arrow: EMP2 expression in epithelial cells & arrowhead: EMP2 staining of ova, inset.
Figure 10:
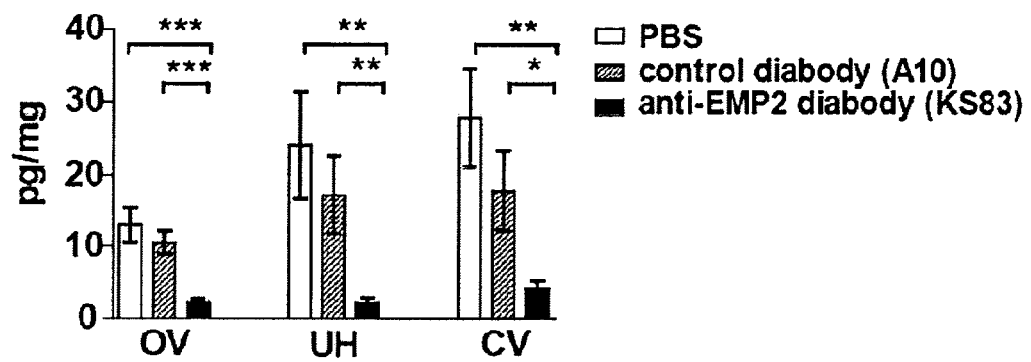
FIG. 10: FGT tissues from mice pretreated as above were collected 4 days after infection, homogenized and the supernatant collected following filtration through 0.22 μm filters and stored at −80° C. pending the ELISA assay. Protein ELISA for IFNγ was performed using a commercial kit (eBioscience). IFNγ protein levels were determined and expressed as pg per milligram of tissue collected. Data are expressed as the mean±SD of picograms IFNγ per mg of protein. Brackets indicate statistical significance, *p<0.05, Student's t-test, n=16/grp.
Figure 11:
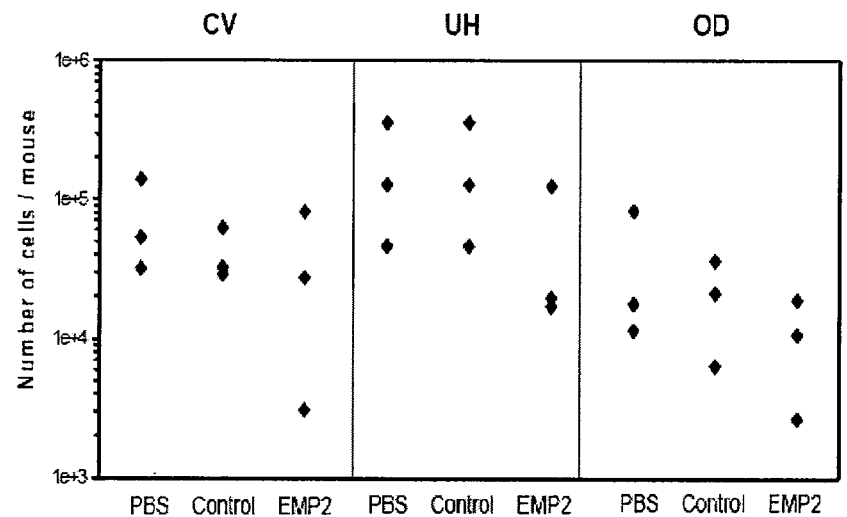
FIG. 11: Mice were pretreated with diabodies or vehicle and infected as above. GT were collected 4 days later, treated with collagenase and stained with CD4, CD3, Ly6G and CD45. Each data point is a pool of 10 mice showing the numbers of or Ly6G+CD4-CD3-neutrophils.
Figure 12:
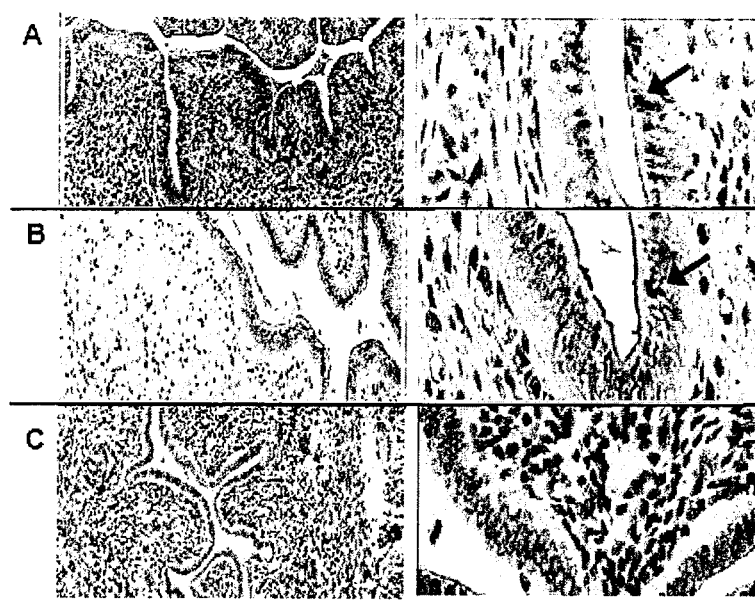
FIG. 12: Formalin-fixed, paraffin-embedded sections of UH were obtained from ovarectomized CF-1 mice 3 days after receiving progesterone (A) estradiol (B), or no hormonal treatment (C) and IHC stained with anti-murine EMP2 sera. Magnification left (100×) and right (400×).
Figure 13:
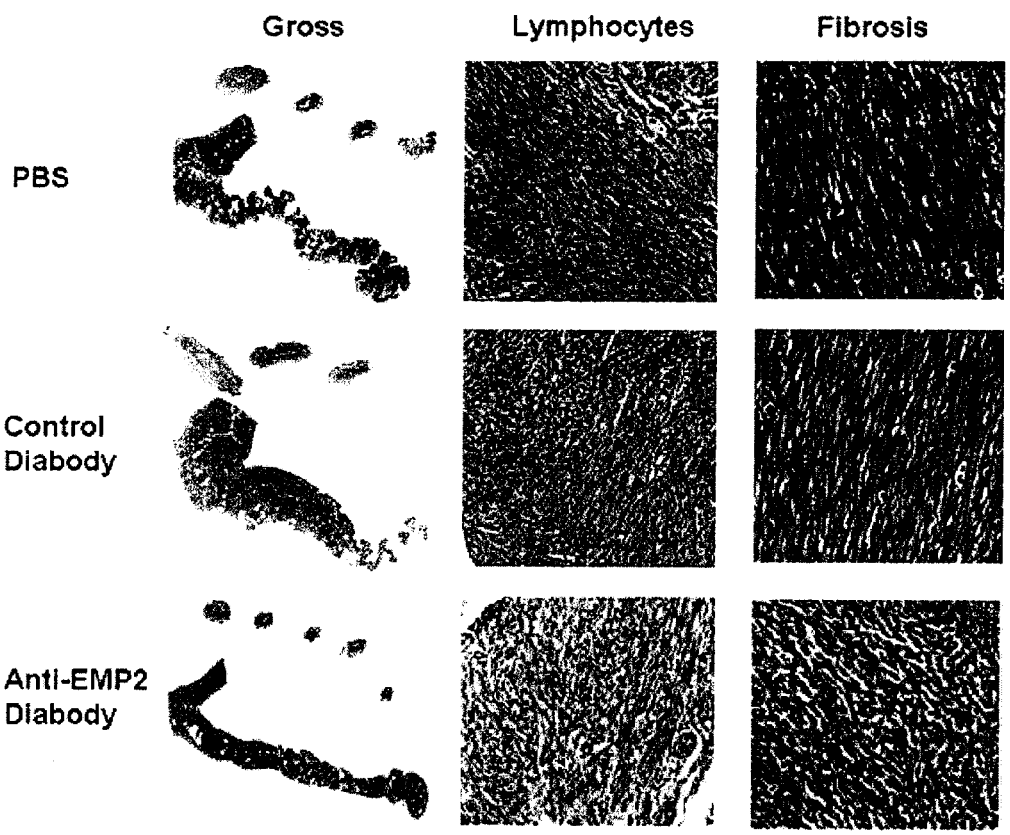
FIG. 13: Effects of no antibody (PBS), control diabody, and test antibody in the tissue indicated. Five-week old BALB/c mice were intravaginally pre-treated for 30 min with PBS, control diabody (A10), or anti-EMP2 diabody (KS49), prior to the infection with *C. muridarum* (MoPn). Left, gross pathology at day 14; Middle, histopathology with hematoxylin and eosin at day 3 (200× magnification). Note recruitment of lymphocyte aggregates (arrows) and fibrosis (arrowheads). Right, histopathology (200× magnification) with trichrome stain, where blue indicates collagen deposition related to fibrosis.
Figure 14:
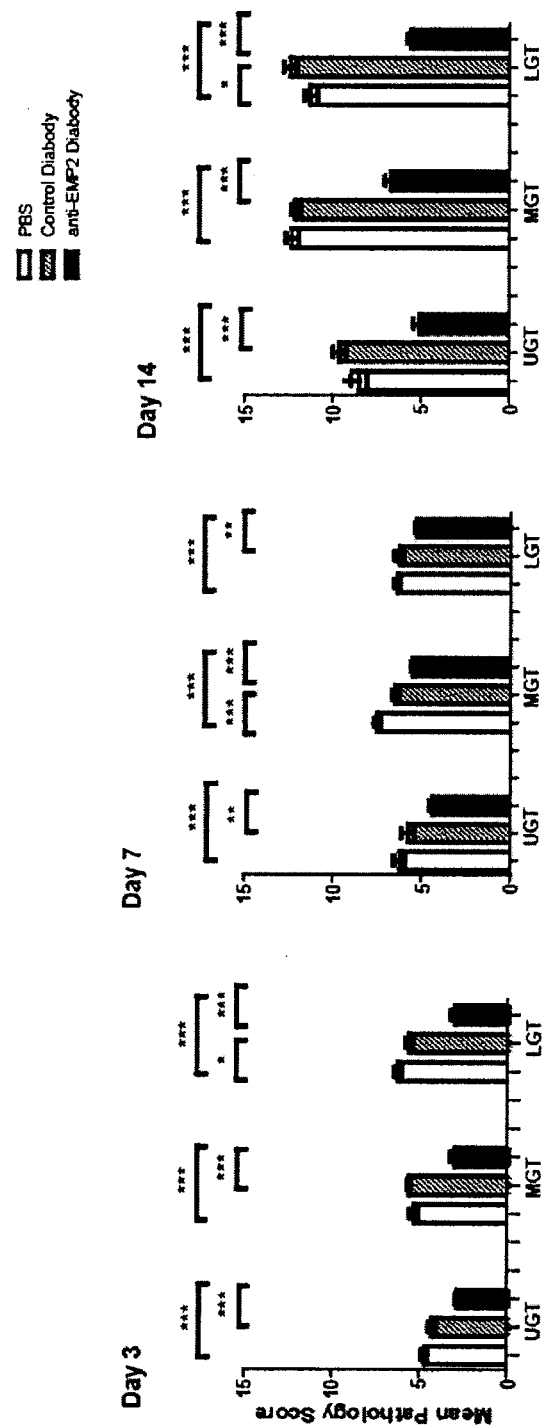
FIG. 14: Effects of no antibody (PBS), control diabody, and test antibody in the tissues indicated. Five-week old BALB/c mice were intravaginally pre-treated for 30 min with PBS, control diabody (A10), or anti-EMP2 diabody (KS49), prior to the infection with *C. muridarum* (MoPn). Genital tracts were obtained at day 3, 7, and 14 after infection, and divided into oviduct (UGT), uterine horn (MGT), and cervico-vaginal (LGT) segments. Histologic sections from each segment were quantitatively scored from 10-20 mice; mean±SEM are shown. Student's t test comparisons are shown (*, p<0.05; ***, p<0.001).

EMP2 is expressed on epithelial cells of the murine FGT in vivo (Shimazaki et al., *Microbes Infect* 9:1003-10 (2007); Wadehra et al., *Dev Biol* 287:336-45 (2005)) and ligation with anti-EMP2 diabody may reduce infectivity by modulating EMP2 expression. To determine whether pretreatment with anti-EMP2 modulates expression within the FGT, immunohistochemical staining (IHC) staining was next performed. As shown in FIG. 9, mice vaginally pretreated with anti-EMP2 diabody showed reduced and altered expression of EMP2 using IHC detection of EMP2 within formalin-fixed, paraffin-embedded sections of FGT compared to control diabody treated mice. Vaginal pretreatment with anti-EMP2 diabody (KS83) reduced the overall expression of EMP2 on epithelial cells as compared to epithelial cells from control diabody pretreated mice (FIG. 9). The diabody was able to reach the oviducts (OD) as EMP2 pretreatment also reduced expression on epithelial cells, however the ova which are adjacent to oviduct tissue serve as a positive internal control as they intensely express EMP2 (FIG. 9E inset, arrowhead) even in anti-EMP2 diabody pretreated mice. Interestingly, anti-EMP2 treatment reduced expression on the apical surface of epithelial cells (FIGS. 9C & D, arrows).

Immune Parameters are Reduced by Blocking the Interaction of EMP2 with MoPn.

Pretreatment with anti-EMP2 diabody was also able to reduce activation of the local immune response reflecting a reduction in vaginal infection. The cytokine IFNγ is secreted by CD4, CD8 and NK cells which appear in GT tissue shortly after infection (Maxion et al., Infect Immun 72: 6330-40 (2004); Darville et al., *Infect Immun* 69: 3556-61 (2001)). Expression of IFNγ by ELISA was examined using a commercially available kit (eBioscience) in homogenized regions of the GT obtained 4 days after pretreatment and infection as described above. As shown in FIG. 10, analysis revealed a significant decrease in IFNγ protein levels in the CV and UH regions, markedly diminished levels within the OD and suggesting that cells secreting IFNγ were reduced in number in mice pretreated with EMP2 diabody.

Fewer leukocytes ought to be present in the FGT of mice pretreated with an anti-EMP2 diabody to reflect the reduction in bacterial burden and decrease in local IFNγ protein levels. Accordingly, the number of polymorphonuclear (PMN) cells in pretreated mice early after infection was evaluated. Briefly, mice were pretreated with anti-EMP2, diabody control or vehicle and infected as above. Early after infection (4 days), FGT tissues were collected and stained for cell surface markers of immune cells. As shown in FIG. 11, diminished numbers of PMN (Ly6G/C+CD3−CD4−) were observed, particularly in the OD of the FGT. This observation confirms the ability of anti-EMP2 diabody treatment to reduce MoPn tissue burden and IFNγ levels in vivo which results in diminished numbers of accumulating leukocytes. Taken together, the results show that pretreatment of mice with anti-EMP2 diabodies significantly reduces the ascending bacterial burden and inflammatory response in the FGT following infection with *C. muridarum*. Accordingly, masking EMP2 in individuals should reduce *C. trachomatis* genital infection and pelvic inflammatory disease and sexual transmission.

Our laboratory recently found that progesterone treatment results in increased EMP2 surface expression (data not shown) and pretreatment of mice with progesterone is understood to increase the susceptibility to infection in vivo. The effect on surface expression of EMP2 of progesterone therapy in vivo was next tested.

Ovariectomized female mice were treated with daily injections of 100 ng per mouse of 17β estradiol or 1 mg per mouse of progesterone dissolved in 100 μL of sesame oil, or sesame oil alone (Sigma). Mice were euthanized at various time points and genital tracts were processed for IHC using mEMP2 antisera or control rabbit serum. Tissue blocks were immunostained using an antigen retrieval technique according to published protocol, and rabbit polyclonal antibodies generated against mouse EMP2 were previously described (Wang et al., Blood 97:3890-3895 (2001)). In ovariectomized mice EMP2 is not detected by immunohistochemistry, however treatment with progesterone or estradiol, induces expression of EMP2 on the endoplasmic reticulum and golgi of the luminal and glandular epithelium at 3 days (FIG. 12). Expression is observed on the apical plasma membrane at an earlier time point (not shown). Taken together, these data support a novel approach, GT tissue pretreatment with anti-EMP2 to reduce MoPn genital infection.

Each publication, patent application, patent, and other reference cited herein is incorporated by reference in its entirety to the extent that it is not inconsistent with the present disclosure. In particular, all publications cited herein are incorporated herein by reference in their entirety for the purpose of describing and disclosing the methodologies, reagents, and tools reported in the publications that might be used in connection with the invention. Nothing herein is to be construed as an admission that the invention is not entitled to antedate such disclosure by virtue of prior invention.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of reducing *Chlamydia trachomatis* infection efficiency in a human subject, said method comprising topically administering to the subject a therapeutically effective amount of an Epithelial membrane protein 2 (EMP2) *Chlamydia* inhibitor to the subject, wherein the EMP2 *Chlamydia* inhibitor is an EMP2 siRNA capable of inhibiting the expression of a protein of SEQ ID NO: 1, wherein the EMP2 siRNA has a nucleic acid sequence with complete identity to the nucleic acid sequence of SEQ ID NO:3 or its complement and is from about 20 to 30 nucleotides in length, whereby the ability of *Chlamydia trachomatis* to bind a host cell in the subject is inhibited.

2. The method of claim 1, wherein the EMP2 siRNA is from 20 to 25 nucleotides in length.

3. The method of claim 1, wherein the inhibitor inhibits the entry of the *Chlamydia trachomatis* into a cell whose expression of EMP2 is inhibited by the inhibitor.

4. The method of claim 1, wherein the EMP2 siRNA is capable of folding into a short hairpin siRNA.

5. A method of reducing *Chlamydia trachomatis* infection efficiency in a human subject, said method comprising topically administering to a human subject in need thereof a therapeutically effective amount of an epithelial membrane protein 2 (EMP2) siRNA from about 20 to 30 nucleotides in length and having a nucleic acid sequence with complete identity to the nucleic acid sequence of SEQ ID NO:3 or its complement wherein the inhibitor inhibits the entry of the *Chlamydia trachomatis* into a cell.

6. The method of claim 5, wherein the EMP2 siRNA is from 20 to 25 nucleotides in length.

7. The method of claim 5, wherein the EMP2 siRNA is capable of folding into a short hairpin siRNA.

8. The method of claim 5, wherein the administration is intravaginal.

9. The method of claim 5, wherein the administration is ocular.

10. The method of claim 1, wherein the administration is intravaginal.

11. The method of claim 1, wherein the administration is ocular.

* * * * *